(12) United States Patent
Neuman et al.

(10) Patent No.: US 7,582,615 B2
(45) Date of Patent: Sep. 1, 2009

(54) ANTISENSE ANTIVIRAL COMPOUND AND METHOD FOR TREATING ARENAVIRUS INFECTION

(75) Inventors: Benjamin Neuman, Brightwell-Cum-Sotwell (GB); David A. Stein, Corvallis, OR (US); Michael Buchmeier, Encinitas, CA (US); Patrick L. Iversen, Corvallis, OR (US)

(73) Assignees: AVI Biopharma, Inc., Corvallis, OR (US); The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 11/715,572

(22) Filed: Mar. 7, 2007

(65) Prior Publication Data

US 2007/0274957 A1   Nov. 29, 2007

Related U.S. Application Data

(60) Provisional application No. 60/780,228, filed on Mar. 7, 2006.

(51) Int. Cl.
  *A01N 43/04* (2006.01)
  *A61K 31/70* (2006.01)
  *C07H 21/02* (2006.01)
  *C07H 21/04* (2006.01)
  *C12Q 1/68* (2006.01)
  *C12P 19/34* (2006.01)

(52) U.S. Cl. .................. 514/44; 536/23.1; 536/24.3; 536/24.33; 536/24.5; 435/6; 435/91.1; 435/325; 435/375

(58) Field of Classification Search .................. 514/44; 435/6, 91.1, 325, 375; 536/23.1, 24.3, 24.33, 536/24.5
See application file for complete search history.

(56) References Cited

U.S. PATENT DOCUMENTS

| 5,034,506 | A | 7/1991 | Summerton et al. |
| 5,142,047 | A | 8/1992 | Summerton et al. |
| 5,166,315 | A | 11/1992 | Summerton et al. |
| 5,185,444 | A | 2/1993 | Summerton et al. |
| 5,217,866 | A | 6/1993 | Summerton et al. |
| 5,506,337 | A | 4/1996 | Summerton et al. |
| 5,521,063 | A | 5/1996 | Summerton et al. |
| 5,580,767 | A | 12/1996 | Cowsert et al. |
| 5,698,685 | A | 12/1997 | Summerton et al. |

(Continued)

OTHER PUBLICATIONS

Neuman et al. Journal of Virology, 2005 vol. 79:9665-9676.*

(Continued)

*Primary Examiner*—Sean McGarry
*Assistant Examiner*—Terra Cotta Gibbs
(74) *Attorney, Agent, or Firm*—King & Spalding LLP

(57) ABSTRACT

The invention provides antisense antiviral compounds and methods of their use and production in inhibition of growth of viruses of the Arenaviridae family and in the treatment of a viral infection. The compounds are particularly useful in the treatment of Arenavirus infection in a mammal. The antisense antiviral compounds are substantially uncharged morpholino oligonucleotides have a sequence of 12-40 subunits, including at least 12 subunits having a targeting sequence that is complementary to a region associated with viral RNA sequences within a 19 nucleotide region of the 5'-terminal regions of the viral RNA, viral complementary RNA and/or mRNA identified by SEQ ID NO:1.

8 Claims, 8 Drawing Sheets

U.S. PATENT DOCUMENTS

| | | |
|---|---|---|
| 6,365,351 B1 | 4/2002 | Iversen |
| 6,677,153 B2 | 1/2004 | Iversen |
| 6,784,291 B2 | 8/2004 | Iversen et al. |
| 6,828,105 B2 | 12/2004 | Stein et al. |
| 6,841,542 B2 | 1/2005 | Bartelmez et al. |
| 7,049,431 B2 | 5/2006 | Iversen et al. |
| 7,094,765 B1 | 8/2006 | Iversen et al. |

OTHER PUBLICATIONS

Agrawal et al. Molecular Medicine Today, 2000 vol. 6:72-81.*
Branch, AD. TIBS, 1998 vol. 23:45-50.*
Tamm et al. Tthe Lancet, 2001 vol. 358:489-497.*
Gewirtz et al. Proc. Natl. Acad. Sci., 1996 vol. 93:3161-3163.*
Nielsen, PE. Gene Therapy, 2005 vol. 12:956-957.*
Agrawal et al. *Proc Natl Acad Sci U S A.*, 87(4):1401-5 (1990).
Blommers et al., *Nucleic Acids Res.*, 22(20):4187-94 (1994).
Bonham et al., *Nucleic Acids Res.*, 23(7):1197-203 (1995).
Boudvillain et al., *Biochemistry* 36(10):2925-31 (1997).
Cross et al., "Solution structure of an RNA x DNA hybrid duplex containing a 3'-thioformacetal linker and an RNA A-tract." *Biochemistry*, 36(14): 4096-107 (1997).
Ding, D., et al., *Nucleic Acids Res* 24(2):354-60, (1996).
Egholm et al., "PNA hybridizes to complementary oligonucleotides obeying the Watson-Crick hydrogen-bonding rules." *Nature*, 365(6446): 566-8 (1993).
Felgner et al., *PNAS*, 84(21): 7413-7 (1987).
Gait et al., *J. Chem. Soc.*, 0(14):1684-1686 (1974).
Gee et al., *Antisense Nucleic Acid Drug Dev* 8(2):103-11 (1998).
Lesnikowski et al., "Octa(thymidine methanephosphonates) of partially defined stereochemistry: synthesis and effect of chirality at phosphorus on binding to pentadecadeoxyriboadenylic acid." *Nucleic Acids Res.*, 18(8): 2109-15 (1990).
Mertes, M. P. and E. A. Coats (1969). "Synthesis of carbonate analogs of dinucleosides. 3'-Thymidinyl 5'-thymidinyl carbonate, 3'-thymidinyl 5'-(5-fluoro-2'-deoxyuridinyl) carbonate, and 3'-(5-fluoro-2'-deoxyuridinyl) 5'-thymidinyl carbonate." *J Med Chem.*, 12(1): 154-7.
Meyer et al., *Curr. Top. Microbiol. Immunol.*, 262:139-157 (2002).
Moulton, H. M., M. H. Nelson, et al., *Bioconjug Chem* 15(2): 290-9 (2004).
Nelson et al., "Arginine-rich peptide conjugation to morpholino oligomers: effects on antisense activity and specificity." *Bioconjug Chem.*, 16(4): 959-66 (2005).
Polyak et al., *Journal of Virology*, 69(5):3211-3215 (1995).
Summerton, J. and D. Weller, "Morpholino antisense oligomers: design, preparation, and properties.", *Antisense Nucleic Acid Drug Dev.*, 7(3): 187-95 (1997).
Barton, L. L., M. B. Mets, et al. (2002). "Lymphocytic choriomeningitis virus:emerging fetal teratogen." *Am J Obstet Gynecol*, 187(6):1715-6 (2002).
Phillips, MI, Antisense Therapeutics: A Promise Waiting to be Fulfilled, *Methods in Molecular Medicine*, 106:3-10 (2005).
Schiavone et al., *Current Pharmaceutical Design*, 20:769-784 (2004).

* cited by examiner

L-Segment

| SEQ ID NO: | | |
|---|---|---|
| 15 | NC006572 LASV | CGCACCCGGATCCTAGGC |
| 16 | NC006574 MOPV | CGCACAGTGGATCCTAGGC |
| 17 | NC004297 LASV | CGCACCCGGATCCTAGGC |
| 18 | NC006313 SABV | CGCACAGTGGATCCTAGGC |
| 19 | NC005082 GTOV | CGCACAGTGGATCCTAGGC |
| 20 | NC005080 JUNV | CGCACAGTGGATCCTAGGC |
| 21 | NC005079 MACV | CGCACAGTGGATCCTAGGC |
| 22 | NC004292 TCRV | CGCACCGGAGTGGATCCTAGGC |
| 23 | NC005897 PIRV | CGCACAGTGGATCCTAGGC |
| 24 | NC004291 LCMV | CGCACCGGAGGATCCTAGGC |
| 25 | NC006439 PICV | CGCACCGAGGATCCTAGGC |

S-Segment

| SEQ ID NO: | | |
|---|---|---|
| 26 | NC006573 MOPV | CGCACCGGGATCCTAGGC |
| 27 | NC004294 LCMV | CGCACCCGGATCCTAGGC |
| 28 | NC006447 PICV | CGCACAGTGGATCCTAGGC |
| 29 | NC005894 PIRV | CGCACAGTGATCCTAGGC |
| 30 | NC005081 JUNV | CGCACAGTGGATCCTACCC |
| 31 | NC005078 MACV | CGCACAGTGGATCCTAGGC |
| 32 | NC005077 GTOV | CGCACAGTGGATCCTAGGC |
| 33 | NC006317 SABV | CGCACCCGGATCCTAGGC |
| 34 | NC004296 LASV | CGCACAGTGGATCCTAGGC |

Fig. 3

S-Segment RNA:
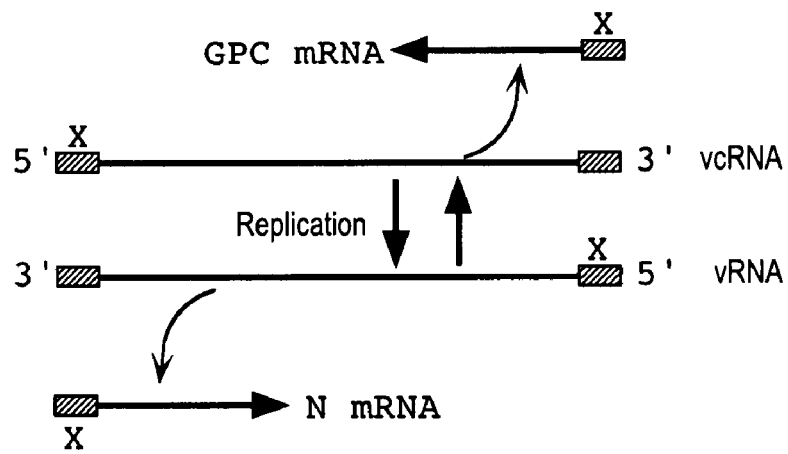
L-Segment RNA:
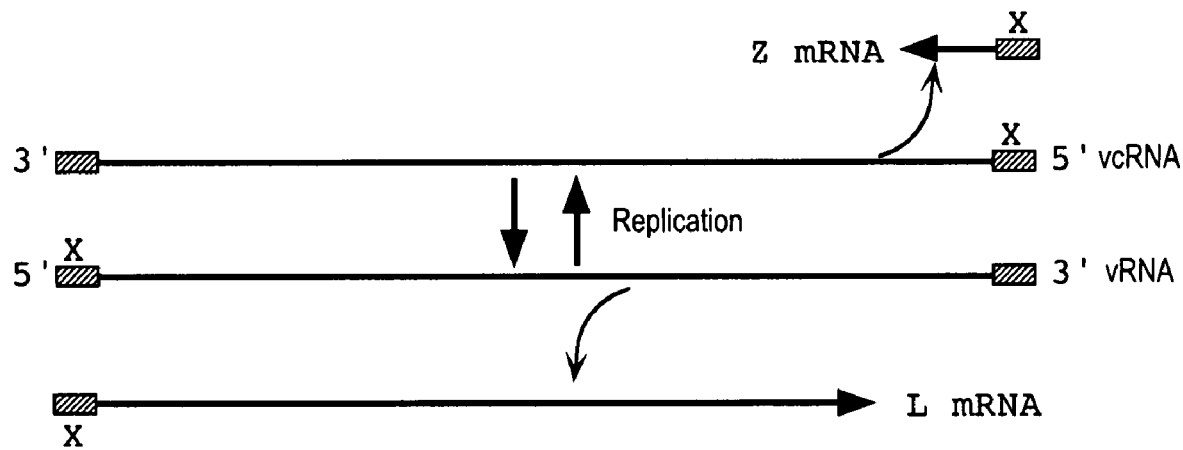
Fig. 4

ANTISENSE ANTIVIRAL COMPOUND AND METHOD FOR TREATING ARENAVIRUS INFECTION

This application claims priority to U.S. Provisional Application No. 60/780,228, entitled Antisense Antiviral Compound And Method For Treating Arenavirus Infection, filed Mar. 7, 2006, which is hereby incorporated by reference in its entirety.

This invention was made, in part, with U.S. Government support under Grant Nos. T32 NS-041219, AI-050840, and AI-065359, awarded by the National Institutes of Health to co-inventors M. Buchmeier and B. Neuman. As to the rights of M. Buchmeier and B. Neuman, or any assignee thereof, in this invention, the U.S. Government has certain rights in the invention.

FIELD OF THE INVENTION

This invention relates to antisense oligonucleotide compounds for use in treating an arenavirus infection and antiviral treatment methods employing the compounds.

REFERENCES

Agrawal, S., S. H. Mayrand, et al (1990). "Site-specific excision from RNA by RNase H and mixed-phosphate-backbone oligodeoxynucleotides." *Proc Natl Acad Sci USA* 87(4):1401-5.

Barton, L. L., M. B. Mets, et al. (2002). "Lymphocytic choriomeningitis virus:emerging fetal teratogen." *Am J Obstet Gynecol* 187(6):1715-6.

Biommers, M. J., U. Pieles, et al. (1994). "An approach to the structure determination of nucleic acid analogues hybridized to RNA. NMR studies of a duplex between 2'-OMe RNA and an oligonucleotide containing a single amide backbone modification." *Nucleic Acids Res* 22(20):4187-94.

Bonham, M. A., S. Brown, et al. (1995). "An assessment of the antisense properties of RNase H-competent and steric-blocking oligomers." *Nucleic Acids Res* 23(7):1197-203.

Boudvillain, M., M. Guerin, et al. (1997). "Transplatin-modified oligo(2'-O-methyl ribonucleotide)s:a new tool for selective modulation of gene expression." *Biochemistry* 36(10):2925-31.

Cross, C. W., J. S. Rice, et al. (1997). "Solution structure of an RNA×DNA hybrid duplex containing a 3'-thioformacetal linker and an RNA A-tract." *Biochemistry* 36(14):4096-107.

Ding, D., S. M. Grayaznov, et al. (1996). "An oligodeoxyribonucleotide N3'-->P5' phosphoramidate duplex forms an A-type helix in solution." *Nucleic Acids Res* 24(2):354-60.

Egholm, M., O. Buchardt, et al. (1993). "PNA hybridizes to complementary oligonucleotides obeying the Watson-Crick hydrogen-bonding rules." *Nature* 365(6446):566-8.

Felgner, P. L., T. R. Gadek, et al. (1987). "Lipofection:a highly efficient, lipid-mediated DNA-transfection procedure." *Proc Natl Acad Sci USA* 84(21):7413-7.

Gait, M. J., A. S. Jones, et al. (1974). "Synthetic-analogues of polynucleotides XII. Synthesis of thymidine derivatives containing an oxyacetamido- or an oxyformamido-linkage instead of a phosphodiester group." *J Chem Soc [Perkin* 1] 0(14):1684-6.

Gee, J. E., I. Robbins, et al. (1998). "Assessment of high-affinity hybridization, RNase H cleavage, and covalent linkage in translation arrest by antisense oligonucleotides."*Antisense Nucleic Acid Drug Dev* 8(2):103-11.

Knipe, D. M., P. M. Howley, et al. (2001). *Fields Virology*, Lippincott.

Lesnikowski, Z. J., M. Jaworska, et al. (1990). "Octa(thymidine methanephosphonates) of partially defined stereochemistry:synthesis and effect of chirality at phosphorus on binding to pentadecadeoxyriboadenylic acid." *Nucleic Acids Res* 18(8):2109-15.

Mertes, M. P. and E. A. Coats (1969). "Synthesis of carbonate analogs of dinucleosides. 3'-Thymidinyl 5'-thymidinyl carbonate, 3'-thymidinyl 5'-(5-fluoro-2'-deoxyuridinyl)carbonate, and 3'-(5-fluoro-2'-deoxyuridinyl) 5'-thymidinyl carbonate." *J Med Chem* 12(1):154-7.

Meyer, B. J., J. C. de la Torre, et al. (2002). "Arenaviruses: genomic RNAs, transcription, and replication." *Curr Top Microbiol Immunol* 262:139-57.

Moulton, H. M., M. H. Nelson, et al. (2004). "Cellular uptake of antisense morpholino oligomers conjugated to arginine-rich peptides." *Bioconjug Chem* 15(2):290-9.

Nelson, M. H., D. A. Stein, et al. (2005). "Arginine-rich peptide conjugation to morpholino oligomers:effects on antisense activity and specificity." *Bioconjug Chem* 16(4): 959-66.

Polyak, S. J., S. Zheng, et al. (1995). "5' termini of Pichinde arenavirus S RNAs and mRNAs contain nontemplated nucleotides." *J Virol* 69(5):3211-5.

Strauss, J. H. and E. G. Strauss (2002). *Viruses and Human Disease*. San Diego, Academic Press.

Summerton, J. and D. Weller (1997). "Morpholino antisense oligomers:design, preparation, and properties." *Antisense Nucleic Acid Drug Dev* 7(3):187-95.

BACKGROUND OF THE INVENTION

The family Arenaviridae contains a single genus, Arenavirus, consisting of at least 16 currently recognized species that can be divided into Old World and New World viruses as shown in Table 1. Because of their association with individual rodent species, arenavirus species are restricted to that of their host. Rodents that have been distributed widely by humans also spread their associated virus as exemplified by the prototypic Arenavirus lymphocytic choriomeningitis virus (LCMV). LCMV is an Old World virus that is associated with the house mouse *Mus domesticus* and *Mus musculus* and is found throughout Europe and the Americas.

The most significant Arenavirus species with regards to pathogenic human infectious disease are the Old World viruses LCMV and Lassa virus (LASV) and the New World viruses Junin virus (JUNV) also known as Argentine Hemorrhagic Fever virus (AHF), Machupo virus (MACV) also known as Bolivian Hemorrhagic Fever virus (BHF), Guanarito virus (GTOV) also known as Venezuelan Hemorrhagic Fever virus (VHF), Sabia virus (SABV) and Whitewater Arroyo virus (WWAV).

LCMV is less virulent for man than the other Arenaviruses and cases usually present as a viral meningitis although deeper neurologic involvement is evident in a minority of cases, perhaps 10% or fewer in naturally observed outbreaks. Encephalitis has been diagnosed in 5% to 34% of hospitalized patients with documented LCMV. Full recovery is usual, although occasional deaths do occur (Knipe, Howley et al. 2001). A more significant risk to humans is the threat of fetal LCMV infections. It is becoming increasingly apparent that LCMV is an important cause of fetal abnormalities in the United States (Barton, Mets et al. 2002).

Lassa virus is endemic to West Africa and causes between 100,000 to 300,000 cases a year (Strauss and Strauss 2002) and the mortality of hospitalized cases is 15-20% (Knipe, Howley et al. 2001). Fatal Lassa virus infection is a relentless disease with the progression of symptoms culminating in the onset of shock and death. Clinical manifestations include aseptic meningitis, encephalitis, global encephalopathy with seizures, and more subtle neurologic problems. Lassa virus is also known to cause unusually high fetal mortality.

The New World Arenaviruses are very important disease agents that cause large outbreaks of hemorrhagic fever with high mortality rates. The number of cases is increasing with development and expanding populations that bring humans in closer association with the rodent reservoirs.

An effective attenuated virus vaccine against Junin virus (AHF) has been developed and is used widely in populations at risk of infection. However, no vaccines are in use for the other Arenaviruses. Passive immunotherapy against some Arenaviruses has shown promise but this approach is complicated due to limited availability and the need to treat with large volumes of plasma, typically two to three units.

The only existing antiviral drug used to treat infections by the viruses described above is the guanosine analog ribavarin which has shown to be moderately effective against a limited subset of the arenavirus species. Ribavarin penetrates poorly into the cerebral spinal fluid which limits its potential as an LCMV antiviral drug.

All Arenaviruses form stable, infectious aerosols and have been important causes of laboratory infections and deaths and consequently are manipulated under BSL-4 containment. The potential for many of these viruses to be used as agents of bioterrorism or biowarfare is widely accepted and as a result LCMV, JUNV, MACV, GTOV and LASV are listed as Category A Pathogens by the National Institute of Allergy and Infectious Disease (NIAID).

Thus, there remains a need for a more effective antiviral therapy against several members of the Arenaviridae family.

SUMMARY OF THE INVENTION

The invention includes, in one aspect, a method of inhibiting viral infection in mammalian cells by a species in the Arenaviridae family. The method includes the steps of exposing the cells to an antisense oligonucleotide compound, thereby to form a heteroduplex structure (i) composed of the virus' vRNA, vcRNA and/or mRNA strands and the oligonucleotide compound, and (ii) characterized by a Tm of dissociation of at least 45° C.

The oligonucleotide compound is characterized by:
(i) a substantially uncharged, nuclease-resistant backbone,
(ii) capable of uptake by mammalian host cells,
(iii) containing between 12-40 nucleotide bases, and
(iv) having a targeting sequence of at least 12 subunits complementary to SEQ ID NO:1 in either the vRNA, vcRNA and/or mRNA strands of the virus The compound to which the host cells are exposed may be composed of morpholino subunits and phosphorus-containing intersubunit linkages joining a morpholino nitrogen of one subunit to a 5' exocyclic carbon of an adjacent subunit. The morpholino subunits may be joined by phosphorodiamidate linkages having the structure:

where $Y_1=O$, $Z=O$, Pj is a purine or pyrimidine base-pairing moiety effective to bind, by base-specific hydrogen bonding, to a base in a polynucleotide, and X is alkyl, alkoxy, thioalkoxy, amino or alkyl amino, including dialkylamino.

The oligonucleotide compound to which the cells are exposed may have a sequence complementary to SEQ ID NO:1, such as one of the sequences identified by SEQ ID NOS:2-5. The compound may be conjugated to an arginine-rich polypeptide effective to promote uptake of the compound into infected host cells. Exemplary arginine-rich polypeptides have one of the sequences identified as SEQ ID NOS: 7-12.

For use in treating a mammalian subject infected by a virus of the Arenaviridae family, the compound is administered to the subject in a pharmaceutically effective amount. Compound administration may be continued until a significant reduction in viral infection or the symptoms thereof is observed. The subject may be treated with a second anti-viral compound before, after, or during treatment with the oligonucleotide compound.

For use in treating a mammalian subject at risk of infection by a virus of the Arenaviridae family, the compound is administered to the subject in an amount effective to inhibit infection of subject host cells by the virus.

In another aspect, the invention includes an oligonucleotide compound for use in inhibiting viral infection in mammalian cells by a virus of the Arenaviridae family. The compound is characterized by:
(i) a substantially uncharged, nuclease-resistant backbone,
(ii) capable of uptake by mammalian host cells,
(iii) containing between 12-40 nucleotide bases,
(iv) having a targeting sequence of at least 12 subunits complementary to SEQ ID NO:1; and
(v) capable of binding to the virus' vRNA, vcRNA and/or mRNA strands to form a heteroduplex structure having by a Tm of dissociation of at least 45° C.

The compound may be composed of morpholino subunits and phosphorus-containing intersubunit linkages joining a morpholino nitrogen of one subunit to a 5' exocyclic carbon of an adjacent subunit. The morpholino subunits may be joined by phosphorodiamidate linkages having the structure:

where $Y_1=O$, $Z=O$, Pj is a purine or pyrimidine base-pairing moiety effective to bind, by base-specific hydrogen bonding, to a base in a polynucleotide, and X is alkyl, alkoxy, thioalkoxy, amino or alkyl amino, including dialkylamino.

The oligonucleotide compound may have one of the sequences identified by SEQ ID NOS:2-5. The compound may be conjugated to an arginine-rich polypeptide effective to promote uptake of the compound into infected host cells. Exemplary arginine-rich polypeptides have one of the sequences identified as SEQ ID NOS:6-12.

The compound may be formulated in combination with another anti-viral compound.

These and other objects and features of the invention will become more fully apparent when the following detailed description of the invention is read in conjunction with the accompanying drawings.

BRIEF DESCRIPTION OF THE FIGURES

FIG. 3 shows the sequence conservation across a broad spectrum of Arenaviruses for the 19 nucleotide 5' terminal region of both the L- and S-segment RNA strands represented by the combined sequence identified by SEQ ID NO:1 (SEQ ID NOs:15-34).

FIG. 4 is a schematic diagram showing the ambisense coding strategy for the S- and L-segments of a typical Arenavirus, the genome organization of the S- and L-segments and the replicative and transcriptional events in the viral life-cycle.

DETAILED DESCRIPTION OF THE INVENTION

I. Definitions

The terms below, as used herein, have the following meanings, unless indicated otherwise:

The terms "oligonucleotide analog" refers to an oligonucleotide having (i) a modified backbone structure, e.g., a backbone other than the standard phosphodiester linkage found in natural oligo- and polynucleotides, and (ii) optionally, modified sugar moieties, e.g., morpholino moieties rather than ribose or deoxyribose moieties. The analog supports bases capable of hydrogen bonding by Watson-Crick base pairing to standard polynucleotide bases, where the analog backbone presents the bases in a manner to permit such hydrogen bonding in a sequence-specific fashion between the oligonucleotide analog molecule and bases in a standard polynucleotide (e.g., single-stranded RNA or single-stranded DNA). Preferred analogs are those having a substantially uncharged, phosphorus containing backbone. An oligonucleotide analog is also referred to herein as an oligonucleotide or oligonucleotide compound or oligonucleotide analog compound.

A substantially uncharged, phosphorus containing backbone in an oligonucleotide analog is one in which a majority of the subunit linkages, e.g., between 60-100%, typically at least 80% of its linkages, are uncharged at physiological pH, and contain a single phosphorous atom. The analog contains between 8 and 40 subunits, typically about 8-25 subunits, and preferably about 12 to 25 subunits. The analog may have exact sequence complementarity to the target sequence or near complementarity, as defined below.

A "subunit" of an oligonucleotide analog refers to one nucleotide (or nucleotide analog) unit of the analog. The term may refer to the nucleotide unit with or without the attached intersubunit linkage, although, when referring to a "charged subunit", the charge typically resides within the intersubunit linkage (e.g. a phosphate or phosphorothioate linkage).

A "morpholino oligonucleotide analog" or "morpholino oligonucleotide compound" is an oligonucleotide analog composed of morpholino subunit structures of the form shown in FIGS. 1A-1D where (i) the structures are linked together by phosphorus-containing linkages, one to three atoms long, joining the morpholino nitrogen of one subunit to the 5' exocyclic carbon of an adjacent subunit, and (ii) $P_i$ and $P_j$ are purine or pyrimidine base-pairing moieties effective to bind, by base-specific hydrogen bonding, to a base in a polynucleotide. The purine or pyrimidine base-pairing moiety is typically adenine, cytosine, guanine, uracil or thymine. The synthesis, structures, and binding characteristics of morpholino oligomers are detailed in U.S. Pat. Nos. 5,698,685, 5,217,866, 5,142,047, 5,034,506, 5,166,315, 5,521,063, and 5,506,337, all of which are incorporated herein by reference.

Figure 1A:
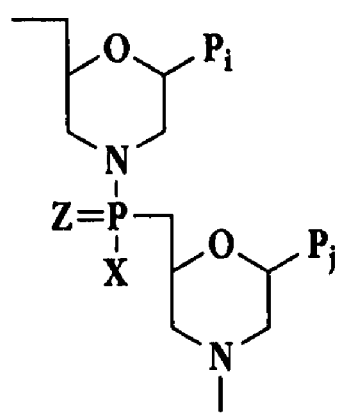
FIGS. 1A-1D show the repeating subunit segment of exemplary morpholino oligonucleotides, designated A through D.
Figure 1B:
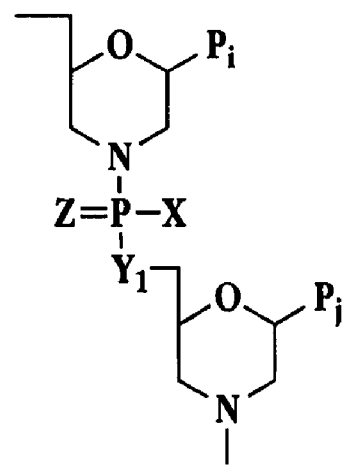

The subunit and linkage shown in FIG. 1B are used for six-atom repeating-unit backbones, as shown in FIG. 1B (where the six atoms include: a morpholino nitrogen, the connected phosphorus atom, the atom (usually oxygen) linking the phosphorus atom to the 5' exocyclic carbon, the 5' exocyclic carbon, and two carbon atoms of the next morpholino ring). In these structures, the atom $Y_1$ linking the 5' exocyclic morpholino carbon to the phosphorus group may be sulfur, nitrogen, carbon or, preferably, oxygen. The X moiety pendant from the phosphorus is any stable group which does not interfere with base-specific hydrogen bonding. Preferred X groups include fluoro, alkyl, alkoxy, thioalkoxy, and alkyl amino, including cyclic amines, all of which can be variously substituted, as long as base-specific bonding is not disrupted. Alkyl, alkoxy and thioalkoxy preferably include 1-6 carbon atoms. Alkyl amino preferably refers to lower alkyl($C_1$ to $C_6$) substitution, and cyclic amines are preferably 5- to 7-membered nitrogen heterocycles optionally containing 1-2 additional heteroatoms selected from oxygen, nitrogen, and sulfur. Z is sulfur or oxygen, and is preferably oxygen.

A preferred morpholino oligomer is a phosphorodiamidate-linked morpholino oligomer, referred to herein as a PMO. Such oligomers are composed of morpholino subunit structures such as shown in FIG. 1B, where X=$NH_2$, NHR, or $NR_2$ (where R is lower alkyl, preferably methyl), Y=O, and Z=O, and $P_i$ and $P_j$ are purine or pyrimidine base-pairing moieties effective to bind, by base-specific hydrogen bonding, to a base in a polynucleotide. Also preferred are structures having an alternate phosphorodiamidate linkage, where, in FIG. 1B, X=lower alkoxy, such as methoxy or ethoxy, Y=NH or NR, where R is lower alkyl, and Z=O.

The term "substituted", particularly with respect to an alkyl, alkoxy, thioalkoxy, or alkylamino group, refers to replacement of a hydrogen atom on carbon with a heteroatom-containing substituent, such as, for example, halogen, hydroxy, alkoxy, thiol, alkylthio, amino, alkylamino, imino, oxo(keto), nitro, cyano, or various acids or esters such as carboxylic, sulfonic, or phosphonic. It may also refer to replacement of a hydrogen atom on a heteroatom (such as an amine hydrogen) with an alkyl, carbonyl or other carbon containing group.

As used herein, the term "Arenavirus" refers to one or more viral species belonging to the Arenaviridae family and specifically viruses categorized as either Old World Arenaviruses or New World Arenaviruses within the Arenavirus genus.

As used herein, the term "target" refers to a viral RNA region, and specifically, to a region identified by SEQ ID NO:1 at the 5'-termini of either the viral RNA (vRNA), viral complementary RNA (vcRNA) or viral mRNA of a member of the Arenaviridae described herein.

The term "target sequence" refers to a portion of the target RNA against which the oligonucleotide analog is directed, that is, the sequence to which the oligonucleotide analog will hybridize by Watson-Crick base pairing of a complementary sequence.

The term "targeting sequence" is the sequence in the oligonucleotide analog that is complementary (meaning, in addition, substantially complementary) to the target sequence in the RNA genome. The entire sequence, or only a portion, of the analog compound may be complementary to the target sequence. For example, in an analog having 20 bases, only 12-14 may be targeting sequences. Typically, the targeting sequence is formed of contiguous bases in the analog, but may alternatively be formed of non-contiguous sequences that when placed together, e.g., from opposite ends of the analog, constitute sequence that spans the target sequence.

Target and targeting sequences are described as "complementary" to one another when hybridization occurs in an antiparallel configuration. A targeting sequence may have "near" or "substantial" complementarity to the target sequence and still function for the purpose of the present invention, that is, still be "complementary." Preferably, the oligonucleotide analog compounds employed in the present invention have at most one mismatch with the target sequence out of 10 nucleotides, and preferably at most one mismatch out of 20. Alternatively, the antisense oligomers employed have at least 90% sequence homology, and preferably at least 95% sequence homology, with the exemplary targeting sequences as designated herein. For purposes of complementary binding to an RNA target, and as discussed below, a guanine base may be complementary to either an adenine or uracil RNA base.

An oligonucleotide analog "specifically hybridizes" to a target polynucleotide if the oligomer hybridizes to the target under physiological conditions, with a $T_m$ substantially greater than 45° C., preferably at least 50° C., and typically 60° C.-80° C. or higher. Such hybridization preferably corresponds to stringent hybridization conditions. At a given ionic strength and pH, the $T_m$ is the temperature at which 50% of a target sequence hybridizes to a complementary polynucleotide. Again, such hybridization may occur with "near" or "substantial" complementary of the antisense oligomer to the target sequence, as well as with exact complementarity.

A "nuclease-resistant" oligomeric molecule (oligomer) refers to one whose backbone is substantially resistant to nuclease cleavage, in non-hybridized or hybridized form; by common extracellular and intracellular nucleases in the body; that is, the oligomer shows little or no nuclease cleavage under normal nuclease conditions in the body to which the oligomer is exposed.

A "heteroduplex" refers to a duplex between an oligonucleotide analog and the complementary portion of a target RNA. A "nuclease-resistant heteroduplex" refers to a heteroduplex formed by the binding of an antisense oligomer to its complementary target, such that the heteroduplex is substantially resistant to in vivo degradation by intracellular and extracellular nucleases, such as RNAse H, which are capable of cutting double-stranded RNA/RNA or RNA/DNA complexes.

A "base-specific intracellular binding event involving a target RNA" refers to the specific binding of an oligonucleotide analog to a target RNA sequence inside a cell. The base specificity of such binding is sequence specific. For example, a single-stranded polynucleotide can specifically bind to a single-stranded polynucleotide that is complementary in sequence.

An "effective amount" of an antisense oligomer, targeted against an infecting Arenavirus, is an amount effective to reduce the rate of replication of the infecting virus, and/or viral load, and/or symptoms associated with the viral infection.

As used herein, the term "body fluid" encompasses a variety of sample types obtained from a subject including, urine, saliva, plasma, blood, spinal fluid, or other sample of biological origin, such as skin cells or dermal debris, and may refer to cells or cell fragments suspended therein, or the liquid medium and its solutes.

The term "relative amount" is used where a comparison is made between a test measurement and a control measurement. The relative amount of a reagent forming a complex in a reaction is the amount reacting with a test specimen, compared with the amount reacting with a control specimen. The control specimen may be run separately in the same assay, or it may be part of the same sample (for example, normal tissue surrounding a malignant area in a tissue section).

"Treatment" of an individual or a cell is any type of intervention provided as a means to alter the natural course of the individual or cell. Treatment includes, but is not limited to, administration of e.g., a pharmaceutical composition, and may be performed either prophylactically, or subsequent to the initiation of a pathologic event or contact with an etiologic agent. The related term "improved therapeutic outcome" relative to a patient diagnosed as infected with a particular virus, refers to a slowing or diminution in the growth of virus, or viral load, or detectable symptoms associated with infection by that particular virus.

An agent is "actively taken up by mammalian cells" when the agent can enter the cell by a mechanism other than passive diffusion across the cell membrane. The agent may be transported, for example, by "active transport", referring to transport of agents across a mammalian cell membrane by e.g. an ATP-dependent transport mechanism, or by "facilitated transport", referring to transport of antisense agents across the cell membrane by a transport mechanism that requires binding of the agent to a transport protein, which then facilitates passage of the bound agent across the membrane. For both active and facilitated transport, the oligonucleotide analog preferably has a substantially uncharged backbone, as defined below. Alternatively, the antisense compound may be formulated in a complexed form, such as an agent having an anionic backbone complexed with cationic lipids or liposomes, which can be taken into cells by an endocytotic mechanism. The analog also may be conjugated, e.g., at its 5' or 3' end, to an arginine-rich peptide, e.g., a portion of the HIV TAT protein, polyarginine, or combinations of arginine and other amino acids including the non-natural amino acids 6-aminohexanoic acid and beta-alanine. Exemplary arginine-rich delivery peptides are listed as SEQ ID NOS:7-12. These exemplary arginine-rich delivery peptides facilitate transport into the target host cell as described (Moulton, Nelson et at 2004; Nelson, Stein et at. 2005).

Rules for the selection of targeting sequences capable of inhibiting replication of Arenaviruses are discussed below.

II. Targeted Viruses

The present invention is based on the discovery that effective inhibition of members of the Arenaviridae family can be achieved with antisense oligonucleotide analog compounds that (i) target the region identified by SEQ ID NO:1 at the 5' terminus of both the S- L-segment RNA strands, and (ii) have physical and pharmacokinetic features which allow effective interaction between the antisense compound and the virus within host cells. In one aspect, the oligomers can be used in treating a mammalian subject infected with the virus.

The invention targets RNA viruses that are members of the Arenaviridae family including members of the Arenavirus genera, the sole genus of the Arenaviridae family. Table 1 is an exemplary list of viruses targeted by the invention as organized by their Old World or New World Arenavirus classification. Various physical, morphological, and biological characteristics of members of the Arenaviridae family can be found, for example, in Textbook of Human Virology, R. Belshe, ed., 2nd Edition, Mosby, 1991, at the Universal Virus Database of the International Committee on Taxonomy of Viruses (ncbi.nlm.nih.gov/ICTVdb/index.htm) and in human virology textbooks (e.g., see (Knipe, Howley et al. 2001) and (Strauss and Strauss 2002)). Some of the key biological characteristics of the Arenaviridae family of viruses are described below.

TABLE 1

Targeted Viruses of the Invention

| Family | Genus | Virus |
|---|---|---|
| Arenaviridae | Arenavirus | Old World Arenaviruses |
| | | Lassa virus (LASV) |
| | | Lymphocytic choriomeningitis virus (LCMV) |
| | | Mopeia virus (MOPV) |
| | | New World Arenaviruses |
| | | Guanarito virus (GTOV) |
| | | Junín virus (JUNV) |
| | | Machupo virus (MACV) |
| | | Pichinide virus (PICV) |
| | | Pirital virus (PIRV) |
| | | Sabiá virus (SABV) |
| | | Tacaribe virus (TCRV) |
| | | Whitewater Arroyo virus (WWAV) |

Genomic Organization of Arenaviruses

All Arenaviruses are enveloped and have a bi-segmented RNA with a unique ambisense genomic organization (Knipe, Howley et al. 2001; Meyer, de la Torre et al. 2002). The genome of Arenaviruses consists of two single-stranded RNA segments designated S (small) and L (large). In virions, the molar ratio of S- to L-segment RNAs is roughly 2:1. The complete S-segment RNA sequence has been determined for several arenaviruses and ranges from 3,366 to 3,535 nucleotides. The complete L- segment RNA sequence has also been determined for several arenaviruses and ranges from 7,102 to 7,279 nucleotides. The 3' terminal sequences of the S and L RNA segments are identical at 17 of the last 19 nucleotides (for the S-segment SEQ ID NO: 13 it is 5'-GCCUAG-GAUCCACUGUGC-3', and for L-segment SEQ ID NO: 14 it is 5'-GCCUAGGAUCCUCGGUGCG-3'). These terminal sequences are conserved among all known arenaviruses as shown in FIG. 3. The 5'-terminal 19 or 20 nucleotides at the beginning of each genomic RNA are imperfectly complementary with each corresponding 3' end. Because of this complementarity, the 3' and 5' termini are thought to base-pair and form panhandle structures. An additional G residue, which would not participate in base-pairing with a corresponding 3'-terminal base, has been detected on the 5' end of some genomic RNAs (Polyak, Zheng et aL 1995). In these cases, the panhandle structures would not contain flush ends, for there would be a single G overhang on the 5' side.

Replication of the infecting virion or viral RNA (vRNA) to form an antigenomic, viral-complementary RNA (vcRNA) strand occurs in the infected cell (FIG. 4). Both the vRNA and vcRNA encode complementary mRNAs and because of that Arenaviruses are classified as ambisense RNA viruses as opposed to either negative- or positive-sense RNA viruses. The ambisense orientation of viral genes are on both the L- and S-segments (FIG. 4). The NP and polymerase genes reside at the 3' end of the S and L vRNA segments, respectively, and are encoded in the conventional negative sense (i.e., they are expressed through transcription of vRNA or genome-complementary mRNAs). The genes located at the 5' end of the S and L vRNA segments, GPC and Z, respectively, are encoded in mRNA sense but there is no evidence that they are translated directly from genomic vRNA. These genes are expressed instead through transcription of genomic-sense mRNAs from antigenomes (i.e., the vcRNA), full-length complementary copies of genomic vRNAs that function as replicative intermediates (FIG. 4).

GenBank reference entries for exemplary viral nucleic acid sequences representing Arenavirus vRNA are listed in Table 2 below. The nucleotide sequence numbers in Table 2 are derived from the Genbank reference for the vcRNA. It will be appreciated that these sequence references are only illustrative of other sequences in the Arenaviridae family, as may be available from available gene-sequence databases or literature or patent resources.

Antisense Oligomer Targets in the Arenavirus Genome

Table 2 lists the antisense targets for a 19-base sequence corresponding to nucleotides 1-19 or 2-20 and contained in the 5'-terminal region of both the S- and L-segments of the listed Arenaviruses. All the viruses listed in Table 2 are human isolates The target sequence (SEQ ID NO:1) is 5'-CGCAC-MGDGGATCCTAGGC-3' where the International Union of Pure and Applied Chemistry (IUPAC) nomenclature for incompletely specified bases are used in the description of the sequence (i.e., "M" for either C or A and "D" for either A, G or T).

An important feature of the present invention is the high degree of sequence conservation between Arenaviruses at the 5' terminus of the vRNA and vcRNA, as shown in FIG. 3. The points where the antisense oligomers of the present invention can exert their antiviral effects are shown schematically in FIG. 4 as indicated by an "X". The targets include the 5' termini of either the S- or L-segment vRNA or vcRNA strands or the 5' termini of any of the four viral mRNAs. As such, the oligomers potentially disrupt viral replication, transcription or translation of viral RNA species.

The prototypic member of the Arenaviridae family is lymphocytic choriomeningitis virus (LCMV). Table 2 lists the corresponding target regions in a number of clinically relevant Arenaviruses and those present in the NCBI Reference Sequence database. Both the Reference Sequence Number (Ref. No.) and the GenBank Accession number (GB No.) are provided. The target homologies for the target region across several Arenaviruses is shown in FIG. 3. The target sequence identified as SEQ ID NO:1 represents a combined target sequence, where the positions indicated by the letter "M" may be either C or A and "D" is either A, G or T.

TABLE 2

Exemplary Human Arenavirus Nucleic Acid Target Sequences

| Virus | Ref. No. | GB No. | Segment | Region | SEQ ID NO |
|---|---|---|---|---|---|
| LASV | NC_004296 | J04324 | S | 1-19 | 34 |
| LASV | NC_004297 | U73034 | L | 1-19 | 17 |
| LCMV | NC_004294 | M20869 | S | 1-19 | 27 |
| LCMV | NC_004291 | J04331 | L | 1-19 | 24 |
| MOPV | NC_006575 | AY772170 | S | 1-19 | 26 |
| MOPV | NC_006574 | AY772169 | L | 1-19 | 16 |
| GTOV | NC_005077 | AY129247 | S | 1-19 | 32 |
| GTOV | NC_005082 | AY358024 | L | 1-19 | 19 |
| JUNV | NC_005081 | AY358023 | S | 1-19 | 30 |
| JUNV | NC_005080 | AY358022 | L | 1-19 | 20 |
| MACV | NC_005078 | AY129248 | S | 1-19 | 31 |
| MACV | NC_005079 | AY358021 | L | 1-19 | 21 |
| PICV | NC_006447 | K02734 | S | 1-19 | 28 |
| PICV | NC_006439 | AF427517 | L | 1-19 | 25 |
| PIRV | NC_005894 | AF485262 | S | 1-19 | 29 |
| PIRV | NC_005897 | AY494081 | L | 1-19 | 23 |
| SABV | NC_006317 | U41071 | S | 1-19 | 33 |
| SABV | NC_006313 | AY358026 | L | 1-19 | 18 |
| TCRV | NC_004293 | M20304 | S | 1-19 | 35 |
| TCRV | NC_004292 | J04340 | L | 1-19 | 22 |

Targeting sequences are designed to hybridize to a region of the target sequence as listed in Table 3. Selected targeting sequences can be made shorter, e.g., 12 bases, or longer, e.g., 40 bases, and include a small number of mismatches, as long as the sequence is sufficiently complementary to hybridize with the target, and forms with the Arenavirus vRNA/vcRNA or mRNA strands, a heteroduplex having a Tm of 45° C. or greater.

More generally, the degree of complementarity between the target and targeting sequence is sufficient to form a stable duplex. The region of complementarity of the antisense oligomers with the target RNA sequence may be as short as 8-11 bases, but is preferably 12-15 bases or more, e.g. 12-20 bases, or 12-25 bases. An antisense oligomer of about 14-15 bases is generally long enough to have a unique complementary sequence in the viral genome. In addition, a minimum length of complementary bases may be required to achieve the requisite binding $T_m$, as discussed below.

Oligomers as long as 40 bases may be suitable, where at least the minimum number of bases, e.g., 8-11, preferably 12-15 bases, are complementary to the target sequence. In general, however, facilitated or active uptake in cells is optimized at oligomer lengths less than about 30, preferably less than 25, and more preferably 20 or fewer bases. For PMO oligomers, described further below, an optimum balance of binding stability and uptake generally occurs at lengths of 14-24 bases.

The oligomer may be 100% complementary to the viral nucleic acid target sequence, or it may include mismatches, e.g., to accommodate variants or increase broad reactivity to different viral species, as long as a heteroduplex formed between the oligomer and viral nucleic acid target sequence is sufficiently stable to withstand the action of cellular nucleases and other modes of degradation which may occur in vivo. Oligomer backbones which are less susceptible to cleavage by nucleases are discussed below. Mismatches, if present, are less destabilizing toward the end regions of the hybrid duplex than in the middle. The number of mismatches allowed will depend on the length of the oligomer, the percentage of G:C base pairs in the duplex, and the position of the mismatch(es) in the duplex, according to well understood principles of duplex stability. Although such an antisense oligomer is not necessarily 100% complementary to the viral nucleic acid target sequence, it is effective to stably and specifically bind to the target sequence, such that a biological activity of the nucleic acid target, e.g., expression of viral protein(s) and/or replication of viral RNA, is modulated.

The oligomer may also incorporate guanine bases in place of adenine when the target nucleotide is a uracil residue. This is useful when the target sequence varies across different viral species and the variation at any given nucleotide residue is either cytosine or uracil. By utilizing guanine in the targeting oligomer at the position of variability, the well-known ability of guanine to base pair with uracil (termed C/U:G base pairing) can be exploited. By incorporating guanine at these locations, a single oligomer can effectively target a wider range of RNA target variability. Similarly, variation at a given nucleotide can be accommodated by inclusion of inosine in the targeting oligomer. Inosine is capable of forming base pairs with any nucleotide in the complementary strand. An example of this is shown in Table 3 as SEQ ID NOS:5 and 6. Although the target sequence shown in FIG. 3 and listed in Table 2 contains T for thymidine, which is the convention for sequence listings, it will be appreciated that because Arenaviruses are RNA viruses, the T residues refer to uracil.

The stability of the duplex formed between the oligomer and the target sequence is a function of the binding $T_m$ and the susceptibility of the duplex to cellular enzymatic cleavage. The $T_m$ of an antisense compound with respect to complementary-sequence RNA may be measured by conventional methods, such as those described by Hames et al., Nucleic Acid Hybridization, IRL Press, 1985, pp. 107-108 or as described in Miyada C. G. and Wallace R. B., 1987, Oligonucleotide hybridization techniques. *Methods Enzymol. Vol.* 154 pp. 94-107. Each antisense oligomer should have a binding $T_m$, with respect to a complementary-sequence RNA, of greater than body temperature and preferably greater than 50° C. $T_m$'s in the range 60-80° C. or greater are preferred. According to well known principles, the $T_m$ of an oligomer compound, with respect to a complementary-based RNA hybrid, can be increased by increasing the ratio of C:G paired bases in the duplex, and/or by increasing the length (in base pairs) of the heteroduplex. At the same time, for purposes of optimizing cellular uptake, it may be advantageous to limit the size of the oligomer. For this reason, compounds that show high $T_m$ (50° C. or greater) at a length of 20 bases or less are generally preferred over those requiring greater than 20 bases for high $T_m$ values.

Table 3 below shows exemplary targeting sequences, in a 5'-to-3' orientation, that are complementary to a broad spectrum of Arenaviruses. The targeting sequences listed below in Table 3 provide a collection of targeting sequences from which targeting sequences may be selected, according to the general class rules discussed above. The CL-trm, LS-trm and SS-trm targeting oligomers (SED ID NOS:2-4, respectively) were used in experiments conducted in support of the invention as described in the Examples and were designed to target specifically Junin-Candid-1. As shown below, the targeting sequences represented by SEQ ID NOS:5 and 6 incorporate inosine ("I") at two positions of sequence variability across a broad range of Arenavirus species.

TABLE 3

Exemplary Antisense Oligomer Targeting Sequences

| PMO | Target Nucleo-tides | GenBank Acc. No. | Targeting Antisense Oligomer (5' to 3') | SEQ ID NO. |
|---|---|---|---|---|
| CL-trm | 1-20 | NC_005080 | CGC CTA GGA TCC CCG GTG CG | 2 |
| LS-trm | 1-21 | NC_005080 | CGC CTA GGA TCC CCG GTG CGC | 3 |
| SS-trm | 1-20 | NC_005081 | GCC TAG GAT CCA CTG TGC GC | 4 |
| PanCL | 1-19 | N/A | GCC TAG GAT CCI CIG TGC G | 5 |
| PanLS | 1-20 | N/A | CGC CTA GGA TCC ICI GTG CG | 6 |

III. Antisense Oligonucleotide Analog Compounds

A. Properties

As detailed above, the antisense oligonucleotide analog compound has a base sequence targeting a region that includes one or more of the following; 1) the 5' untranslated region of either the vRNA, vcRNA or mRNA and; 2) the 5'-terminal 19 bases of the vRNA, vcRNA or mRNA. In addition, the oligomer is able to effectively target infecting viruses, when administered to a host cell, e.g. in an infected mammalian subject. This requirement is met when the oligomer compound (a) has the ability to be actively taken up by mammalian cells, and (b) once taken up, form a duplex with the target RNA with a $T_m$ greater than about 45° C.

As will be described below, the ability to be taken up by cells requires that the oligomer backbone be substantially uncharged, and, preferably, that the oligomer structure is recognized as a substrate for active or facilitated transport across the cell membrane. The ability of the oligomer to form a stable duplex with the target RNA will also depend on the oligomer backbone, as well as factors noted above, the length and degree of complementarity of the antisense oligomer with respect to the target, the ratio of G:C to A:T base matches, and the positions of any mismatched bases. The ability of the antisense oligomer to resist cellular nucleases promotes survival and ultimate delivery of the agent to the cell cytoplasm.

Below are disclosed methods for testing any given, substantially uncharged backbone for its ability to meet these requirements.

B. Active or Facilitated Uptake by Cells

The antisense compound may be taken up by host cells by facilitated or active transport across the host cell membrane if administered in free (non-complexed) form, or by an endocytotic mechanism if administered in complexed form.

In the case where the agent is administered in free form, the antisense compound should be substantially uncharged, meaning that a majority of its intersubunit linkages are uncharged at physiological pH. Experiments carried out in support of the invention indicate that a small number of net charges, e.g., 1-2 for a 15- to 20-mer oligomer, can in fact enhance cellular uptake of certain oligomers with substantially uncharged backbones. The charges may be carried on the oligomer itself, e.g., in the backbone linkages, or may be terminal charged-group appendages. Preferably, the number of charged linkages is no more than one charged linkage per four uncharged linkages. More preferably, the number is no more than one charged linkage per ten, or no more than one per twenty, uncharged linkages. In one embodiment, the oligomer is fully uncharged.

An oligomer may also contain both negatively and positively charged backbone linkages, as long as opposing charges are present in approximately equal number. Preferably, the oligomer does not include runs of more than 3-5 consecutive subunits of either charge. For example, the oligomer may have a given number of anionic linkages, e.g. phosphorothioate or N3'→P5' phosphoramidate linkages, and a comparable number of cationic linkages, such as N,N-diethylenediamine phosphoramidates (Dagle, Littig et al. 2000). The net charge is preferably neutral or at most 1-2 net charges per oligomer.

The antisense compound may also be administered in complexed form, where the complexing agent is typically a polymer, e.g., a cationic lipid, polypeptide, or non-biological cationic polymer, having an opposite charge to any net charge on the antisense compound. Methods of forming complexes, including bilayer complexes, between anionic oligonucleotides and cationic lipid or other polymer components, are well known. For example, the liposomal composition Lipofectin (Felgner, Gadek et al. 1987), containing the cationic lipid DOTMA (N-[1-(2,3-dioleyloxy)propyl]-N,N,N-trimethylammonium chloride) and the neutral phospholipid DOPE (dioleyl phosphatidyl ethanolamine), is widely used. After administration, the complex is taken up by cells through an endocytotic mechanism, typically involving particle encapsulation in endosomal bodies.

The antisense compound may also be administered in conjugated form with an arginine-rich peptide linked covalently to the 5' or 3' end of the antisense oligomer. The peptide is typically 8-16 amino acids and consists of a mixture of arginine, and other amino acids including phenyalanine, cysteine, beta-alanine and 6-aminohexanoic acid. Exemplary arginine-rich delivery peptides are described in the Sequence Listing table as SEQ ID NOS:7-11. The use of arginine-rich peptide-PMO conjugates can be used to enhance cellular uptake of the antisense oligomer (See, e.g. (Moulton, Nelson et al. 2004; Nelson, Stein et al. 2005).

In some instances, liposomes may be employed to facilitate uptake of the antisense oligonucleotide into cells. (See, e.g., Williams, S. A., Leukemia 10(12):1980-1989, 1996; Lappalainen et al., Antiviral Res. 23:119, 1994; Uhlmann et al., antisense oligonucleotides:a new therapeutic principle, Chemical Reviews, Volume 90, No. 4, pages 544-584, 1990; Gregoriadis, G., Chapter 14, Liposomes, Drug Carriers in Biology and Medicine, pp. 287-341, Academic Press, 1979). Hydrogels may also be used as vehicles for antisense oligomer administration, for example, as described in WO 93/01286. Alternatively, the oligonucleotides may be administered in microspheres or microparticles. (See, e.g., Wu, G. Y. and Wu, C. H., J. Biol. Chem. 262:4429-4432, 1987). Alternatively, the use of gas-filled microbubbles complexed with the antisense oligomers can enhance delivery to target tissues, as described in U.S. Pat. No. 6,245,747.

Alternatively, and according to another aspect of the invention, the requisite properties of oligomers with any given backbone can be confirmed by a simple in vivo test, in which a labeled compound is administered to an animal, and a body fluid sample, taken from the animal several hours after the oligomer is administered, assayed for the presence of heteroduplex with target RNA. This method is detailed in subsection D below.

C. Substantial Resistance to RNaseH

Two general mechanisms have been proposed to account for inhibition of expression by antisense oligonucleotides. (See e.g., (Agrawal, Mayrand et al. 1990; Bonham, Brown et al., 1995; Boudvillain, Guerin et al., 1997). In the first, a heteroduplex formed between the oligonucleotide and the viral RNA acts as a substrate for RNaseH, leading to cleavage of the viral RNA. Oligonucleotides belonging, or proposed to belong, to this class include phosphorothioates, phosphotriesters, and phosphodiesters (unmodified "natural" oligonucleotides). Such compounds expose the viral RNA in an oligomer:RNA duplex structure to hydrolysis by RNaseH, and therefore loss of function.

A second class of oligonucleotide analogs, termed "steric blockers" or, alternatively, "RNaseH inactive" or "RNaseH resistant", have not been observed to act as a substrate for RNaseH, and are believed to act by sterically blocking target RNA nucleocytoplasmic transport, splicing or translation. This class includes methylphosphonates (Toulme et al., 1996), morpholino oligonucleotides, peptide nucleic acids (PNA's), certain 2'-O-allyl or 2'-O-alkyl modified oligonucleotides (Bonham, Brown et al. 1995), and N3'→P5' phosphoramidates (Ding, Grayaznov et al. 1996; Gee, Robbins et al. 1998).

A test oligomer can be assayed for its RNaseH resistance by forming an RNA:oligomer duplex with the test compound, then incubating the duplex with RNaseH under a standard assay conditions, as described in Stein et al. After exposure to RNaseH, the presence or absence of intact duplex can be monitored by gel electrophoresis or mass spectrometry.

D. In Vivo Uptake

In accordance with another aspect of the invention, there is provided a simple, rapid test for confirming that a given antisense oligomer type provides the required characteristics noted above, namely, high $T_m$, ability to be actively taken up by the host cells, and substantial resistance to RNaseH. This method is based on the discovery that a properly designed antisense compound will form a stable heteroduplex with the complementary portion of the viral RNA target when administered to a mammalian subject, and the heteroduplex subsequently appears in the urine (or other body fluid). Details of this method are also given in co-owned U.S. patent application Ser. No. 09/736,920, entitled "Non-Invasive Method for Detecting Target RNA" (Non-Invasive Method), the disclosure of which is incorporated herein by reference.

Briefly, a test oligomer containing a backbone to be evaluated, having a base sequence targeted against a known RNA, is injected into a mammalian subject. The antisense oligomer may be directed against any intracellular RNA, including a host RNA or the RNA of an infecting virus. Several hours (typically 8-72) after administration, the urine is assayed for the presence of the antisense-RNA heteroduplex. If heteroduplex is detected, the backbone is suitable for use in the antisense oligomers of the present invention.

The test oligomer may be labeled, e.g. by a fluorescent or a radioactive tag, to facilitate subsequent analyses, if it is appropriate for the mammalian subject. The assay can be in any suitable solid-phase or fluid format. Generally, a solid-phase assay involves first binding the heteroduplex analyte to a solid-phase support, e.g., particles or a polymer or test-strip substrate, and detecting the presence/amount of heteroduplex bound. In a fluid-phase assay, the analyte sample is typically pretreated to remove interfering sample components. If the oligomer is labeled, the presence of the heteroduplex is confirmed by detecting the label tags. For non-labeled compounds, the heteroduplex may be detected by immunoassay if in solid phase format or by mass spectroscopy or other known methods if in solution or suspension format.

When the antisense oligomer is complementary to a virus-specific region of the viral genome (such as those regions of Arenavirus RNA, as described above) the method can be used to detect the presence of a given Arenavirus virus, or reduction in the amount of virus during a treatment method.

E. Exemplary Oligomer Backbones

Examples of nonionic linkages that may be used in oligonucleotide analogs are shown in FIGS. 2A-2G. In these figures, B represents a purine or pyrimidine base-pairing moiety effective to bind, by base-specific hydrogen bonding, to a base in a polynucleotide, preferably selected from adenine, cytosine, guanine, thymidine and uracil. Suitable backbone structures include carbonate (2A, R=O) and carbamate (2A, R=NH$_2$) linkages (Mertes and Coats 1969; Gait, Jones et al. 1974); alkyl phosphonate and phosphotriester linkages (2B, R=alkyl or —O-alkyl) (Lesnikowski, Jaworska et al. 1990); amide linkages (2C) (Biommers, Pieles et al. 1994); sulfone and sulfonamide linkages (2D, R$_1$, R$_2$=CH$_2$); and a thioformacetyl linkage (2E) (Cross, Rice et al. 1997). The latter is reported to have enhanced duplex and triplex stability with respect to phosphorothioate antisense compounds (Cross, Rice et al. 1997). Also reported are the 3'-methylene-N-methylhydroxyamino compounds of structure 2F.

Peptide nucleic acids (PNAs) are analogs of DNA in which the backbone is structurally homomorphous with a deoxyribose backbone, consisting of N-(2-aminoethyl) glycine units to which pyrimidine or purine bases are attached. PNAs containing natural pyrimidine and purine bases hybridize to complementary oligonucleotides obeying Watson-Crick base-pairing rules, and mimic DNA in terms of base pair recognition (Egholm, Buchardt et al., 1993). The backbone of PNAs are formed by peptide bonds rather than phosphodiester bonds, making them well-suited for antisense applications. The backbone is uncharged, resulting in PNA/DNA or PNA/RNA duplexes which exhibit greater than normal thermal stability. PNAs are not recognized by nucleases or proteases.

A preferred oligomer structure employs morpholino-based subunits bearing base-pairing moieties, joined by uncharged linkages, as described above. Especially preferred is a substantially uncharged phosphorodiamidate-linked morpholino oligomer, such as illustrated in FIGS. 1A-1D. Morpholino oligonucleotides, including antisense oligomers, are detailed, for example, in co-owned U.S. Pat. Nos. 5,698,685, 5,217,866, 5,142,047, 5,034,506, 5,166,315, 5,185,444, 5,521,063, and 5,506,337, all of which are expressly incorporated by reference herein.

Important properties of the morpholino-based subunits include: the ability to be linked in a oligomeric form by stable, uncharged backbone linkages; the ability to support a nucleotide base (e.g. adenine, cytosine, guanine, thymidine, uracil or inosine) such that the polymer formed can hybridize with a complementary-base target nucleic acid, including target RNA, with high $T_m$, even with oligomers as short as 10-14 bases; the ability of the oligomer to be actively transported into mammalian cells; and the ability of the oligomer:RNA heteroduplex to resist RNAse degradation.

Exemplary backbone structures for antisense oligonucleotides of the invention include the α-morpholino subunit types are also shown in FIGS. 1A-1D, each linked by an uncharged, phosphorus-containing subunit linkage. FIG. 1A shows a phosphorus-containing linkage which forms the five atom repeating-unit backbone, where the morpholino rings are linked by a 1-atom phosphoamide linkage. FIG. 1B shows a linkage which produces a 6-atom repeating-unit backbone.

In this structure, the atom Y linking the 5' morpholino carbon to the phosphorus group may be sulfur, nitrogen, carbon or, preferably, oxygen. The X moiety pendant from the phosphorus may be fluorine, an alkyl or substituted alkyl, an alkoxy or substituted alkoxy, a thioalkoxy or substituted thioalkoxy, or unsubstituted, monosubstituted, or disubstituted nitrogen, including cyclic structures, such as morpholines or piperidines. Alkyl, alkoxy and thioalkoxy preferably include 1-6 carbon atoms. The Z moieties are sulfur or oxygen, and are preferably oxygen.

Figure 1C:
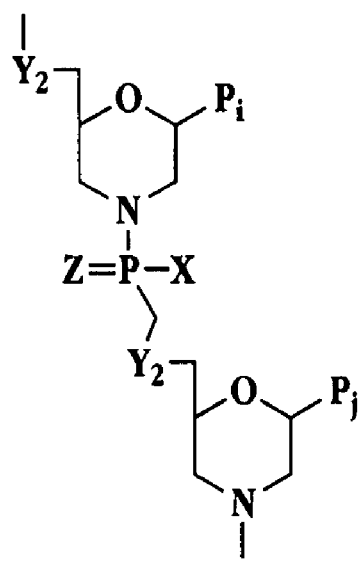
Figure 1D:
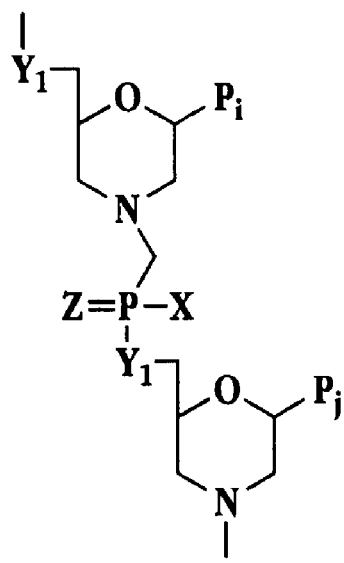

The linkages shown in FIGS. 1C and 1D are designed for 7-atom unit-length backbones. In Structure 1C, the X moiety is as in Structure 1B, and the moiety Y may be methylene, sulfur, or, preferably, oxygen. In Structure 1D, the X and Y moieties are as in Structure 1B. Particularly preferred morpholino oligonucleotides include those composed of morpholino subunit structures of the form shown in FIG. 1B, where $X=NH_2$ or $N(CH_3)_2$, $Y=O$, and $Z=O$ and in FIG. 2G.

Figure 2A:
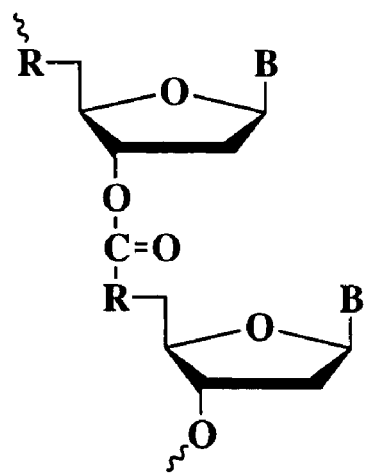
FIGS. 2A-2G show examples of uncharged linkage types in oligonucleotide analogs.
Figure 2B:
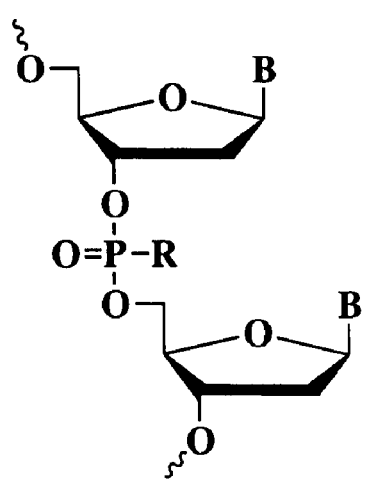
Figure 2C:
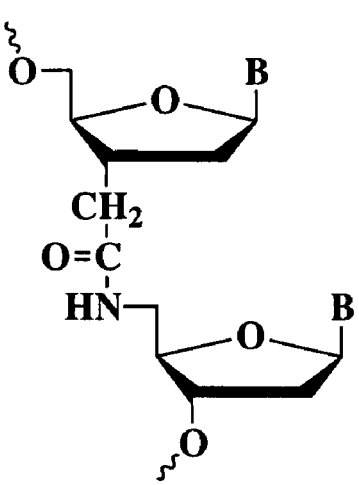
Figure 2D:
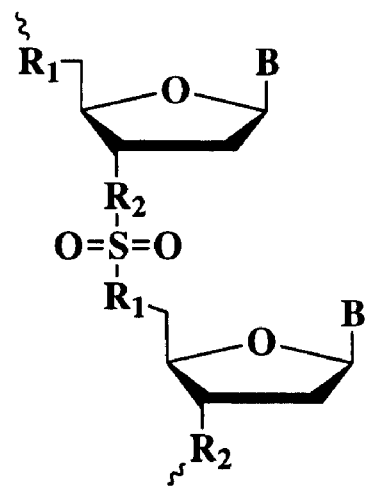
Figure 2E:
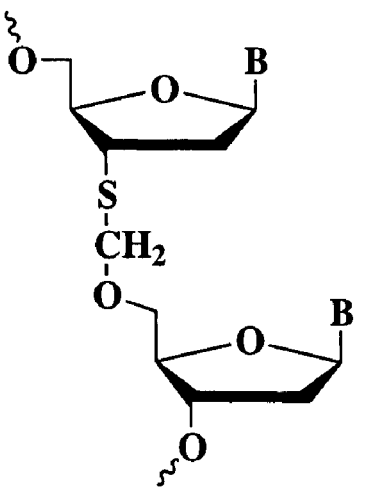
Figure 2F:
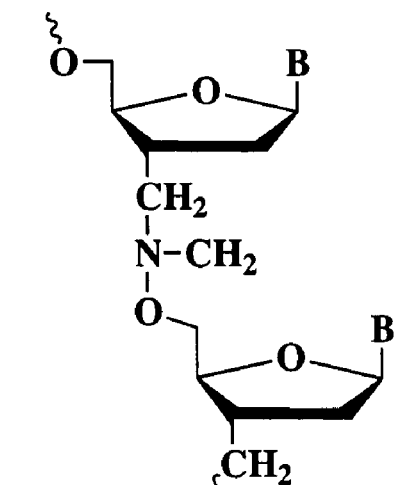
Figure 2G:
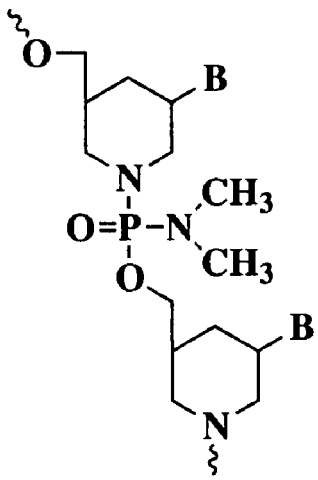
Figure 2H:
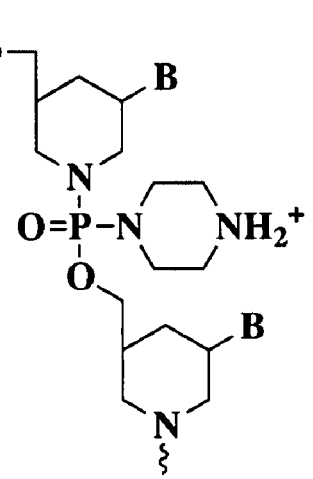
FIG. 2H is an example of a charged, cationic linkage.

As noted above, the substantially uncharged oligomer may advantageously include a limited number of charged linkages, e.g. up to about 1 per every 5 uncharged linkages, more preferably up to about 1 per every 10 uncharged linkages. Therefore a small number of charged linkages, e.g. charged phosphoramidate or phosphorothioate, may also be incorporated into the oligomers. An exemplary cationic linkage structure is shown in FIG. 2H.

The antisense compounds can be prepared by stepwise solid-phase synthesis, employing methods detailed in the references cited above. In some cases, it may be desirable to add additional chemical moieties to the antisense compound, e.g. to enhance pharmacokinetics or to facilitate capture or detection of the compound. Such a moiety may be covalently attached, typically to a terminus of the oligomer, according to standard synthetic methods. For example, addition of a polyethyleneglycol moiety or other hydrophilic polymer, e.g., one having 10-100 monomeric subunits, may be useful in enhancing solubility. One or more charged groups, e.g., anionic charged groups such as an organic acid, may enhance cell uptake. A reporter moiety, such as fluorescein or a radiolabeled group, may be attached for purposes of detection. Alternatively, the reporter label attached to the oligomer may be a ligand, such as an antigen or biotin, capable of binding a labeled antibody or streptavidin. In selecting a moiety for attachment or modification of an antisense oligomer, it is generally of course desirable to select chemical compounds of groups that are biocompatible and likely to be tolerated by a subject without undesirable side effects.

IV. Inhibition of Arenavirus Viral Replication

The antisense compounds detailed above are useful in inhibiting replication of single-stranded, ambi-sense RNA viruses of the Arenaviridae family. In one embodiment, such inhibition is effective in treating infection of a host animal by these viruses. Accordingly, the method comprises, in one embodiment, exposing a mammalian cell infected with the virus with an oligonucleotide antisense compound effective to inhibit the replication of the specific virus. In this embodiment, the cells are exposed to the compound either in vitro or in vivo, where the method is used in the latter case to treat a mammalian subject, e.g., human or domestic animal, infected with a given virus. It is contemplated that the antisense oligonucleotide arrests the growth of the RNA virus in the host. The RNA virus may be decreased in number or eliminated with little or no detrimental effect on the normal growth or development of the host.

In the present invention as described in the Examples, phosphorodiamidate morpholino oligomers (PMOs), designed to hybridize to specific regions of the Junin-Candid Arenavirus 5'-terminal regions, are evaluated for their ability to inhibit viral replication and/or induction of cytopathic effects when used against three different Arenaviruses, LCMV, JUNV and TCRV. The target region is highly conserved within the Arenaviridae family. The PMOs described herein will target most, if not all, Arenavirus species because of the high degree of homology between viral species at the target (SEQ ID NO:1) as shown in FIG. 3.

A. Identification of the Infective Agent

The specific virus causing the infection can be determined by methods known in the art, e.g. serological, genotyping, or cultural methods, or by methods employing the antisense oligomers of the present invention.

Serological identification employs a viral sample or culture isolated from a biological specimen, e.g., stool, urine, cerebrospinal fluid, blood, nasopharyngeal secretions, etc., of the subject. Immunoassay for the detection of virus is generally carried out by methods routinely employed by those of skill in the art, e.g., ELISA or Western blot. In addition, monoclonal antibodies specific to particular viral strains or species are often commercially available.

Culture methods may be used to isolate and identify particular types of virus, by employing techniques including, but not limited to, comparing characteristics such as rates of growth and morphology under various culture conditions.

Genotyping methods include polymerase chain reaction (PCR) methods using genotype-specific primers or genomic sequencing of viral nucleic acid obtained from the infected individual.

Another method for identifying the viral infective agent in an infected subject employs one or more antisense oligomers targeting broad families and/or genera of viruses. Sequences targeting any characteristic viral RNA can be used. The desired target sequences are preferably (i) common to broad virus families/genera, and (ii) not found in humans. Characteristic nucleic acid sequences for a large number of infectious viruses are available in public databases, and may serve as the basis for the design of specific oligomers.

For each plurality of oligomers, the following steps are carried out:(a) the oligomer(s) are administered to the subject; (b) at a selected time after said administering, a body fluid sample is obtained from the subject; and (c) the sample is assayed for the presence of a nuclease-resistant heteroduplex comprising the antisense oligomer and a complementary portion of the viral genome. Steps (a)-(c) are carried for at least one such oligomer, or as many as is necessary to identify the virus or family of viruses. Oligomers can be administered and assayed sequentially or, more conveniently, concurrently. The virus is identified based on the presence (or absence) of a heteroduplex comprising the antisense oligomer and a complementary portion of the viral genome of the given known virus or family of viruses.

Preferably, a first group of oligomers, targeting broad families, is utilized first, followed by selected oligomers complementary to specific genera and/or species and/or strains within the broad family/genus thereby identified. This second group of oligomers includes targeting sequences directed to specific genera and/or species and/or strains within a broad family/genus. Several different second oligomer collections, i.e. one for each broad virus family/genus tested in the first stage, are generally provided. Sequences are selected which are (i) specific for the individual genus/species/strains being tested and (ii) not found in humans.

B. Administration of the Antisense Oligomer

Effective delivery of the antisense oligomer to the target nucleic acid is an important aspect of treatment. In accordance with the invention, routes of antisense oligomer delivery include, but are not limited to, various systemic routes, including oral and parenteral routes, e.g., intravenous, subcutaneous, intraperitoneal, and intramuscular, as well as inhalation, transdermal and topical delivery. The appropriate route may be determined by one of skill in the art, as appropriate to the condition of the subject under treatment. For example, an appropriate route for delivery of a antisense oligomer in the treatment of a viral infection of the skin is topical delivery, while delivery of a antisense oligomer for the treatment of a viral respiratory infection is by inhalation. The oligomer may also be delivered directly to the site of viral infection, or to the bloodstream.

The antisense oligomer may be administered in any convenient vehicle which is physiologically acceptable. Such a composition may include any of a variety of standard pharmaceutically accepted carriers employed by those of ordinary skill in the art. Examples include, but are not limited to, saline, phosphate buffered saline (PBS), water, aqueous ethanol, emulsions, such as oil/water emulsions or triglyceride emulsions, tablets and capsules. The choice of suitable physiologically acceptable carrier will vary dependent upon the chosen mode of administration.

In some instances, liposomes may be employed to facilitate uptake of the antisense oligomer into cells. (See, e.g., Williams, S. A., Leukemia 10(12):1980-1989, 1996; Lappalainen et al., Antiviral Res. 23:119, 1994; Uhlmann et al., antisense oligonucleotides:a new therapeutic principle, Chemical Reviews, Volume 90, No. 4, pages 544-584, 1990; Gregoriadis, G., Chapter 14, Liposomes, Drug Carriers in Biology and Medicine, pp. 287-341, Academic Press, 1979). As described above, the use of arginine-rich cellular delivery peptides conjugated to the antisense oligomer may also be used. Hydrogels may also be used as vehicles for antisense oligomer administration, for example, as described in WO 93/01286. Alternatively, the oligomers may be administered in microspheres or microparticles. (See, e.g., Wu, G. Y. and Wu, C. H., J. Biol. Chem. 262:4429-4432, 1987). Alternatively, the use of gas-filled microbubbles complexed with the antisense oligomers can enhance delivery to target tissues, as described in U.S. Pat. No. 6,245,747.

Sustained release compositions may also be used. These may include semipermeable polymeric matrices in the form of shaped articles such as films or microcapsules.

In one aspect of the method, the subject is a human subject, e.g., a patient diagnosed as having a localized or systemic viral infection. The condition of a patient may also dictate prophylactic administration of an antisense oligomer of the invention, e.g. in the case of a patient who (1) is immunocompromised; (2) is a burn victim; (3) has an indwelling catheter; or (4) is about to undergo or has recently undergone surgery. In one preferred embodiment, the oligomer is a phosphorodiamidate morpholino oligomer, contained in a pharmaceutically acceptable carrier, and is delivered orally. In another preferred embodiment, the oligomer is a phosphorodiamidate morpholino oligomer, contained in a pharmaceutically acceptable carrier, and is delivered intravenously (i.v.).

The antisense compound is generally administered in an amount and manner effective to result in a peak blood concentration of at least 200-400 nM antisense oligomer. Typically, one or more doses of antisense oligomer are administered, generally at regular intervals, for a period of about one to two weeks. Preferred doses for oral administration are from about 1-100 mg oligomer per 70 kg. In some cases, doses of greater than 100 mg oligomer/patient may be necessary. For i.v. administration, preferred doses are from about 0.5 mg to 100 mg oligomer per 70 kg. The antisense oligomer may be administered at regular intervals for a short time period, e.g., daily for two weeks or less. However, in some cases the oligomer is administered intermittently over a longer period of time. Administration may be followed by, or concurrent with, administration of an antibiotic or other therapeutic treatment. The treatment regimen may be adjusted (dose, frequency, route, etc.) as indicated, based on the results of immunoassays, other biochemical tests and physiological examination of the subject under treatment.

C. Monitoring of Treatment

An effective in vivo treatment regimen using the antisense oligonucleotides of the invention may vary according to the duration, dose, frequency and route of administration, as well as the condition of the subject under treatment (i.e., prophylactic administration versus administration in response to localized or systemic infection). Accordingly, such in vivo therapy will often require monitoring by tests appropriate to the particular type of viral infection under treatment, and corresponding adjustments in the dose or treatment regimen, in order to achieve an optimal therapeutic outcome. Treatment may be monitored, e.g., by general indicators of infection, such as complete blood count (CBC), nucleic acid detection methods, immunodiagnostic tests, viral culture, or detection of heteroduplex.

The efficacy of an in vivo administered antisense oligomer of the invention in inhibiting or eliminating the growth of one or more types of RNA virus may be determined from biological samples (tissue, blood, urine etc.) taken from a subject prior to, during and subsequent to administration of the antisense oligomer. Assays of such samples include (1) monitoring the presence or absence of heteroduplex formation with target and non-target sequences, using procedures known to those skilled in the art, e.g., an electrophoretic gel mobility assay; (2) monitoring the amount of viral protein production, as determined by standard techniques such as ELISA or Western blotting, or (3) measuring the effect on viral titer, e.g. by the method of Spearman-Karber. (See, for example, Pari, G. S. et al., Antimicrob. Agents and Chemotherapy 39(5):1157-1161, 1995; Anderson, K. P. et al., Antimicrob. Agents and Chemotherapy 40(9):2004-2011, 1996, Cottral, G. E. (ed) in:Manual of Standard Methods for Veterinary Microbiology, pp. 60-93, 1978).

A preferred method of monitoring the efficacy of the antisense oligomer treatment is by detection of the antisense-RNA heteroduplex. At selected time(s) after antisense oligomer administration, a body fluid is collected for detecting the presence and/or measuring the level of heteroduplex species in the sample. Typically, the body fluid sample is collected 3-24 hours after administration, preferably about 6-24 hours after administering. As indicated above, the body fluid sample may be urine, saliva, plasma, blood, spinal fluid, or other liquid sample of biological origin, and may include cells or cell fragments suspended therein, or the liquid medium and its solutes. The amount of sample collected is typically in the 0.1 to 10 ml range, preferably about 1 ml of less.

The sample may be treated to remove unwanted components and/or to treat the heteroduplex species in the sample to remove unwanted ssRNA overhang regions, e.g. by treatment with RNase. It is, of course, particularly important to remove overhang where heteroduplex detection relies on size separation, e.g., electrophoresis of mass spectroscopy.

A variety of methods are available for removing unwanted components from the sample. For example, since the heteroduplex has a net negative charge, electrophoretic or ion exchange techniques can be used to separate the heteroduplex from neutral or positively charged material. The sample may also be contacted with a solid support having a surface-bound antibody or other agent specifically able to bind the heteroduplex. After washing the support to remove unbound material, the heteroduplex can be released in substantially purified form for further analysis, e.g., by electrophoresis, mass spectroscopy or immunoassay.

V. Examples

The following examples illustrate but are not intended in any way to limit the invention.

A. Materials and Methods

All peptides are custom synthesized by Global Peptide Services (Ft. Collins, Colo.) or at AVI BioPharma (Corvallis, Oreg.) and purified to >90% purity. Phosphorodiamidate morpholino oligomers (PMOs) are synthesized at AVI BioPharma in accordance with known methods, as described, for example, in (Summerton and Weller 1997) and U.S. Pat. No. 5,185,444.

For the examples described below, PMO oligomers are conjugated at the 5' end with an arginine-rich peptide, P007 or (RXR)$_4$XB-PMO (where R is arginine, X is 6-aminohexanoic acid and B is beta-alanine), to enhance cellular uptake as described (U.S. Patent Application 60/466,703 and (Moulton, Nelson et al., 2004; Nelson, Stein et al. 2005). This peptide is also called P007 and listed as SEQ ID NO:8 in the Sequence Listing table. PMOs conjugated to a delivery peptide are called P-PMOs.

Cells and Viruses

Vero-E6 cells were cultured in DMEM containing 10% fetal bovine serum, 0.01 M HEPES, penicillin and streptomycin for general growth and maintenance, or in serum-free medium (VP-SFM; Invitrogen) supplemented with L-glutamine, penicillin and streptomycin during P-PMO studies. Infectious stocks of Junin-Candid#1 (JUNV), Tacaribe virus (TCRV) and lymphocytic choriomeningitis virus-Armstrong (LCMV) were prepared on Vero-E6 cells.

Virus Growth and Titer Reduction Assays

Vero-E6 cells were seeded at a density of 5×10$^5$ cells per 25 cm$^2$ tissue culture flask and allowed to adhere overnight at 37° C., 5% CO$_2$. Cells were pre-treated with 1 ml VP-SFM containing treatment for 6 h, except where stated, as in time-of-addition and time-of-removal experiments. Cells were inoculated with JUNV or LCMV at a multiplicity of 0.1 PFU/cell and placed at 37° C. for 1 h. Inoculum was removed and replaced with fresh VP-SFM with or without P-PMO treatment. Cells in the JUNV and LCMV experiments included with this submission were treated with 15 µM P-PMO in VP-SFM. Cell culture medium was collected, stored and replaced with fresh medium at designated timepoints. Virus in cell culture supernatants was titrated by plaque assay. Cells were fixed with 10% formaldehyde in phosphate buffered saline and stained with 0.1% crystal violet to assess cytopathic effects (CPE).

Plaque Assay

For arenavirus plaque assays, Vero-E6 cells were seeded in 12-well tissue culture plates at 2×10$^5$ cells per well and allowed to adhere overnight at 37° C., 5% CO$_2$. Culture medium was removed and replaced with 0.5 ml of inoculum. Cells were treated as specified, and a 2% fetal bovine serum, 0.7% agarose overlay was applied 1 h after inoculation. After 5d, cells were fixed with 10% formaldehyde in phosphate buffered saline, agarose plugs were removed and cells were stained with 0.1% crystal violet.

Example 1

Inhibition of Junin-Candid-1 virus (JUNV) in Tissue Culture with PMOs that Target the 5' Termini of the vRNA/vcRNA Strands The antiviral activity of Junin-Candid-1-specific PMOs were determined by measuring viral replication and cytopathic effects in JUNV-infected cells. The tests are performed on Vero-E6 cells as described above. Cell monolayers (12-well plates) are seeded 16 to 20 hours prior to treatment with PMO or infection with virus and pretreated pretreated with 1 ml of 15 micromolar P-PMO in serum-free culture medium for 6 h before inoculation. Cells were infected at a multiplicity of infection (MOI) of 0.01 plaque forming units per cell (PFU/cell). Culture medium was collected 96 hours after inoculation and infectious virus was titrated by plaque assay. After collection of the culture medium, cells were fixed with 25% neutral buffered formalin and stained with crystal violet to visualize multinucleate syncytia, a measure of viral-induced cytopathic effects (CPE).

Figure 5:
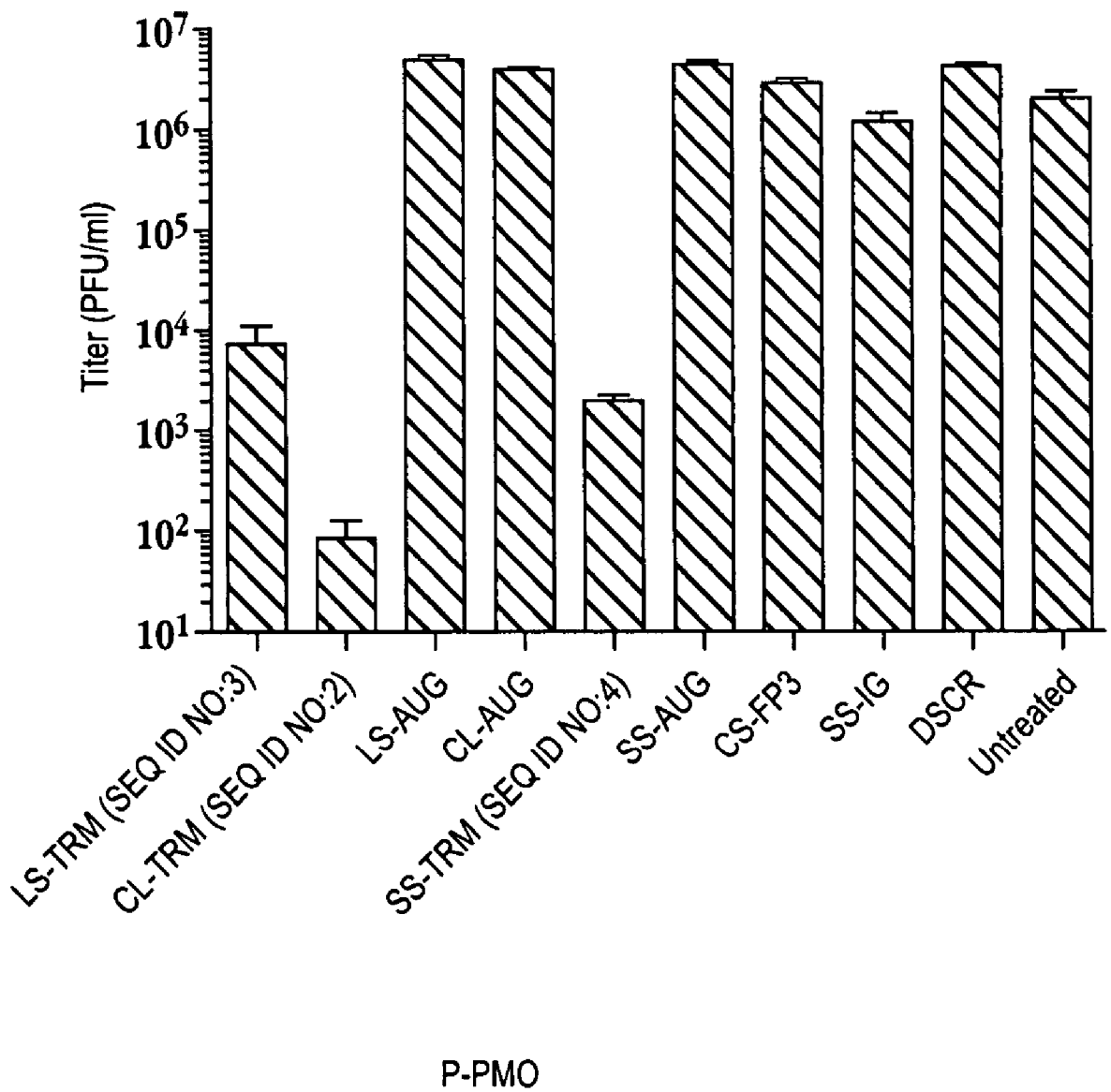
FIG. 5 shows the viral titer reduction when JUNV-infected Vero E6 cells are treated with antisense P-PMO targeting the 5'-termini of vRNA/vcRNA.
Figure 6:
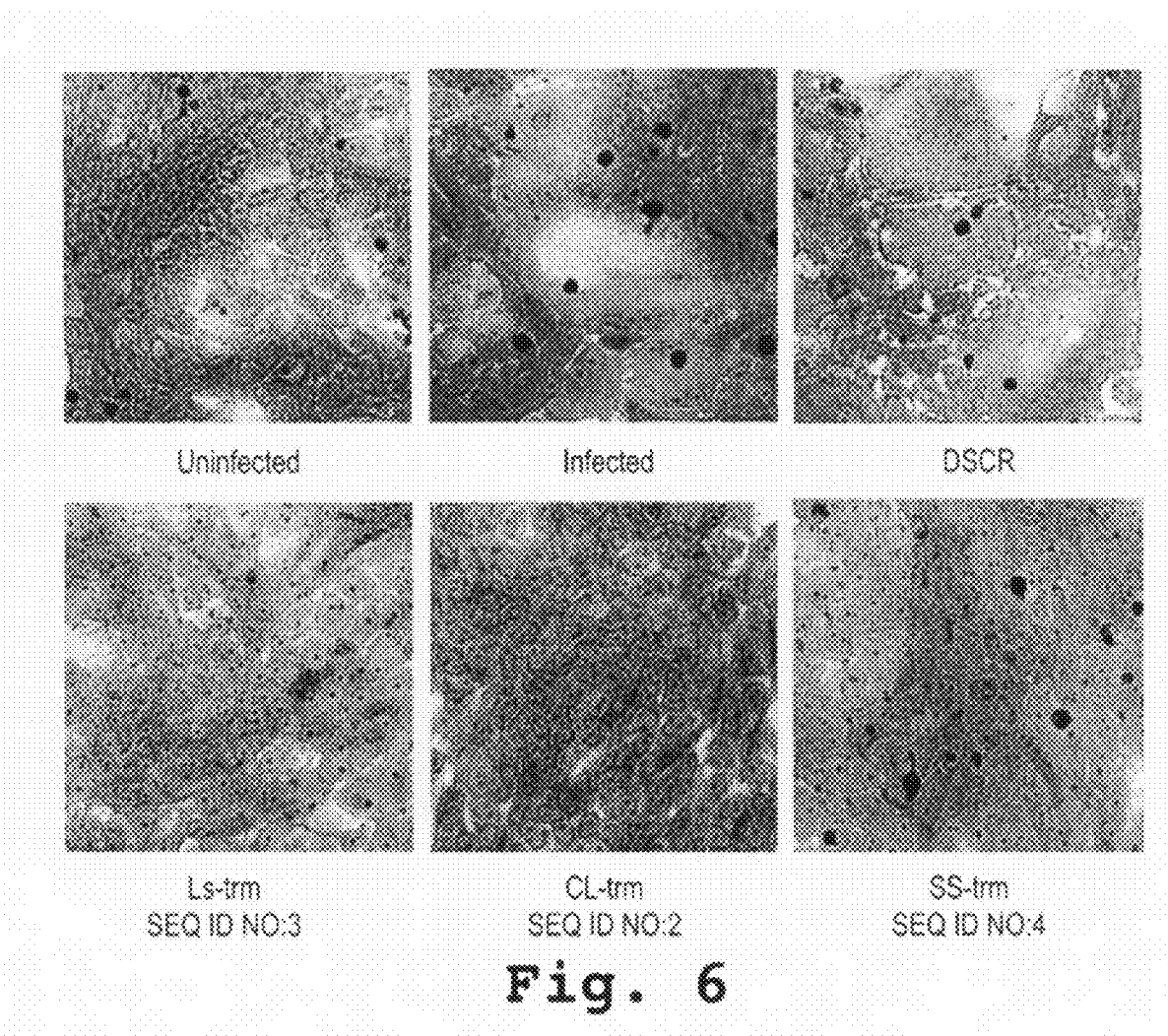
FIG. 6 is a series of photomicrographs showing the reduction of viral cytopathic effects when JUNV-infected Vero E6 cells are treated with antisense P-PMO targeting the 5'-termini of vRNA/vcRNA.

P-PMOs directed at the precise 5'-termini of the vRNA and vcRNA strands, which share a common 19 nt terminal repeat sequence, demonstrated significant inhibitory effects on JUNV replication. As shown in FIG. 5, the terminus-binding P-PMOs (CL-trm, LS-trm and SS-trm, SEQ ID NOS:2-4, respectively) reduced viral titer by 100 to 10000-fold 4d after inoculation compared to viral titers from untreated and randomized P-PMO-treated cells (DSCR) (FIG. 5). The most effective P-PMOs (CL-trm, LS-trm and SS-trm, SEQ ID NOS:2-4, respectively) also reduced CPE, as measured by syncytium formation which results from expression of the viral-encoded GP-C protein on the cell surface, to undetectable levels as shown in FIG. 6.

Example 2

Figure 7:
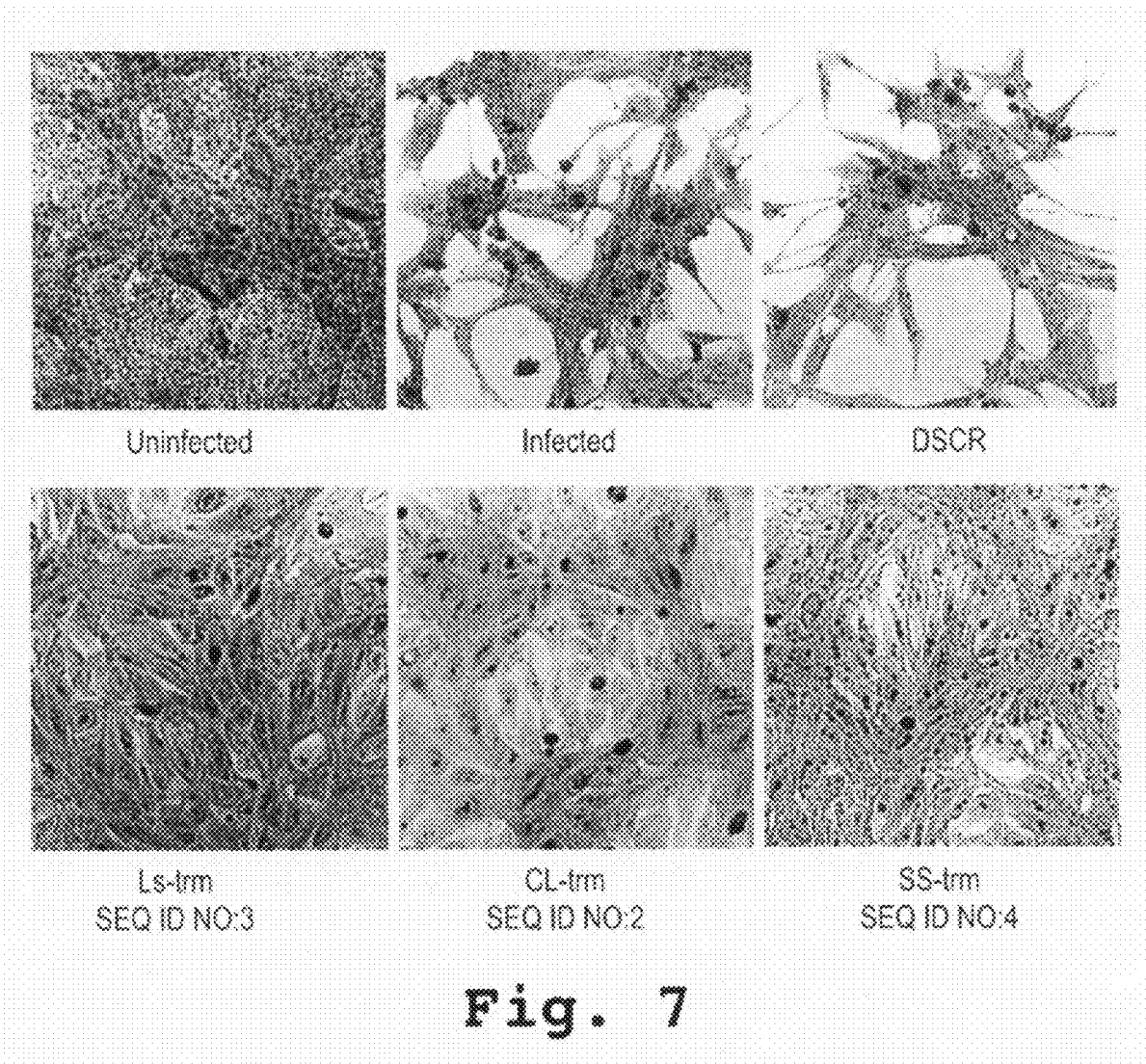
FIG. 7 is a series of photomicrographs showing the reduction of TCRV-induced cytophathic effects when infected Vero E6 cells are treated with antisense P-PMO targeting the 5-termini of vRNA/vcRNA.

Inhibition of Tacaribe Virus (TCRV) Cytopathic Effects in Tissue Culture with PMOs that Target the 5' Termini of the vRNA/vcRNA Strands Antiviral activity against Tacaribe virus (TCRV, another New World arenavirus) was measured by observation of CPE in tissue culture experiments similar to those described for JUNV in Example 1 above. The same series of P007-conjugated P-PMO were selected for these analyses and used to treat Vero-E6 cells under the same conditions described in Example 1 above. Six hours post-treatment with PMO, cells were infected with Tacaribe virus at an MOI of 0.01 pfu/cell. Photomicrographs were taken 96 hours post-infection as shown in FIG. 7. A significant reduction in CPE was observed with the same three P-PMOs (CL-trm, LS-trm and SS-trm, SEQ ID NOS:2-4, respectively) compared to the scramble control P-PMO (DSCR)-treated and untreated TCRV-infected cultures as shown in FIG. 7.

Example 3

Figure 8:
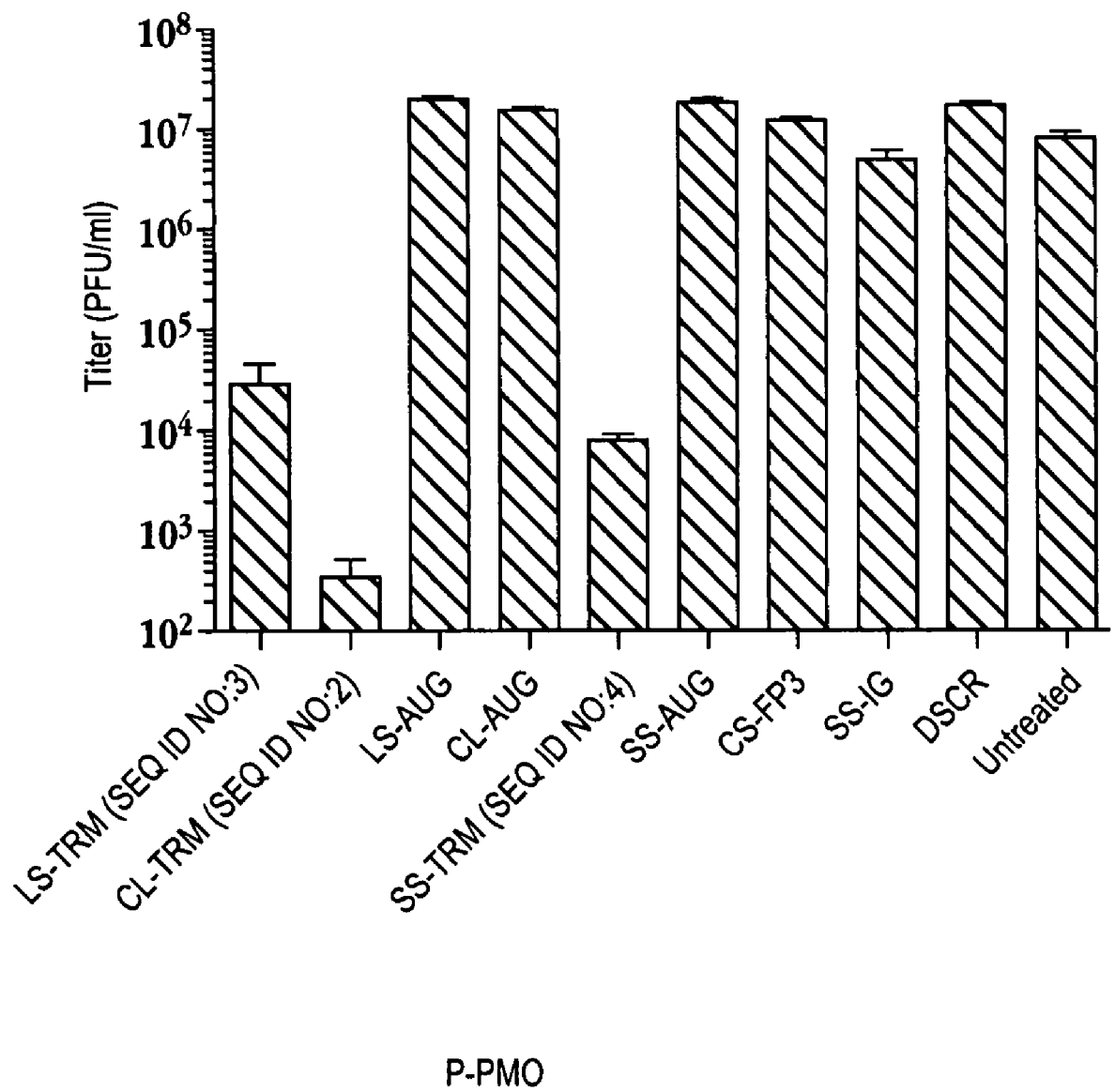
FIG. 8 shows a graph depicting the viral titer reduction (VTR) when LCMV-infected Vero E6 cells are treated with P-PMO targeting the 5'-termini of vRNA/vcRNA.

Inhibition of Lymphocytic Choriomeningitis Virus (LCMV) in Tissue Culture with PMOs that Target the 5' Termini of the vRNA/vcRNA Strands The most effective of the P-PMOs tested against JUNV (CL-trm, LS-trm and SS-trm, SEQ ID NOS:2-4, respectively)

were directed at the conserved genomic 5'-termini. To determine the effectiveness of the same P-PMOs against a distantly related Old World arenavirus, lymphocytic choriomeningitis virus (LCMV) was used in experiments identical to those described in Example 1. P-PMOs directed at the conserved termini (CL-trm, LS-trm and SS-trm, SEQ ID NOS:2-4, respectively) strongly suppressed LCMV proliferation, reducing viral titers by 100 to 100000-fold as shown in FIG. 8. The same negative controls were used as described in Examples 1 and 2, a scramble control sequence (DSCR) and untreated, and demonstrated no inhibition of LCMV replication as shown in FIG. 8. P-PMOs directed to initiation codons and other sequences not conserved among arenaviruses were ineffective at reducing LCMV proliferation (i.e., LS-AUG, CL-AUG, SS-AUG, CS-FP3 and SS-IG). These results support the claim that P-PMOs directed to the genomic termini will have a high probability of inhibiting any strain of arenavirus. The LCMV-Armstrong strain used in these experiments is known to have a two base pair mismatch with each of the P-PMOs that showed antiviral activity, CL-trm, LS-trm and SS-trm, SEQ ID NOS:2-4, respectively.

Certain non-standard nucleotide analogs such as inosine can be included in antisense oligomers to permit binding to target sequences that are heterogeneous at specific sites, as is the case with the arenavirus terminal sequence (e.g., see FIG. 3). Exemplary targeting oligomers that utilize this approach are listed as SEQ ID NOS:5 and 6.

Sequence Listing

| Name | Target Sequences (5' to 3') | SEQ ID NO |
|---|---|---|
| | CGC ACM GDG GAT CCT AGG C | 1 |
| | Oligomer Targeting Sequences (5' to 3') | |
| CL-trm | CGC CTA GGA TCC CCG GTG CG | 2 |
| LS-trm | CGC CTA GGA TCC CCG GTG CGC | 3 |
| SS-trm | GCC TAG GAT CCA CTG TGC GC | 4 |
| PanCL | GCC TAG GAT CCI CIG TGC G | 5 |
| PanLS | CGC CTA GGA TCC ICI GTG CG | 6 |
| | Peptide Sequences (NH₂ to COOH) | |
| P003 | RRRRRRRRRFFAhxβAla | 7 |
| P007 | (RAhxR)₄AhxβAla | 8 |
| P008 | (RAhx)₈βAla | 9 |
| RX4 | (RAhx)₄βAla | 10 |
| RXR2 | (RAhxR)₂AhxβAla | 11 |
| RXR3 | (RAhxR)₃AhxβAla | 12 |

It is claimed:

1. A method of inhibiting viral infection in mammalian cells by an Arenavirus in the Arenaviridae family, comprising
   (a) exposing the cells to an antisense oligonucleotide compound composed of morpholino subunits and phosphorus-containing intersubunit linkages joining a morpholino nitrogen of one subunit to a 5' exocyclic carbon of an adjacent subunit, and characterized by:
   (i) a substantially uncharged, nuclease-resistant backbone,
   (ii) capable of uptake by mammalian host cells,
   (iii) containing between 12-40 nucleotide bases,
   (iv) having a targeting sequence of at least 12 contiguous subunits complementary to SEQ ID NO:1, and
   (v) conjugated to the oligonucleotide, an arginine-rich polypeptide effective to promote uptake of the compound into infected host cells, and
   (b) by said exposing, forming a heteroduplex structure
   (i) composed of the virus' vRNA or vcRNA strand and the oligonucleotide compound, and (ii) characterized by a Tm of dissociation of at least 45° C.

2. The method of claim 1, wherein the morpholino subunits in the oligonucleotide compound to which the host cells are exposed are joined by phosphorodiamidate linkages having the structure:

$$Z=P-X$$
$$\;\;\;|$$
$$\;\;Y_1$$

where $Y_1$=O, Z=O, Pj is a purine or pyrimidine base-pairing moiety effective to bind, by base-specific hydrogen bonding, to a base in a polynucleotide, and X is alkyl, alkoxy, thioalkoxy, amino or alkyl amino, including dialkylamino.

3. The method of claim 1, wherein the oligonucleotide compound to which the cells are exposed has a sequence comprising SEQ ID NO:5.

4. The method of claim 1, wherein the oligonucleotide compound to which the cells are exposed has a sequence comprising SEQ ID NO:2.

5. The method of claim 1, for use in treating a mammalian subject infected by an Arenavirus in the Arenaviridae family, wherein said exposing includes administering to the subject, a pharmaceutically effective amount of the oligonucleotide compound, and which further includes continuing said administering until a significant reduction in viral infection or the symptoms thereof is observed.

6. The method of claim 5, which further includes administering a second anti-viral compound to the subject.

7. The method of claim 1, for use in treating a mammalian subject at risk of infection by an Arenavirus in the Arenaviridae family, wherein said exposing includes administering to the subject, an amount of the oligonucleotide compound effective to inhibit infection of subject host cells by the virus.

8. The method of claim 1, wherein the arginine rich peptide has the sequence identified as SEQ ID NO: 8.

* * * * *

UNITED STATES PATENT AND TRADEMARK OFFICE
CERTIFICATE OF CORRECTION

PATENT NO. : 7,582,615 B2  Page 1 of 1
APPLICATION NO. : 11/715572
DATED : September 1, 2009
INVENTOR(S) : Benjamin Neuman et al.

It is certified that error appears in the above-identified patent and that said Letters Patent is hereby corrected as shown below:

On the Title page Item (73) Assignees should read: AVI Biopharma, Inc. Corvallis, OR (US); The Scripps Research Institute, La Jolla, CA (US)

Signed and Sealed this

Third Day of November, 2009

David J. Kappos
*Director of the United States Patent and Trademark Office*

SEQUENCE LISTING

```
<160> NUMBER OF SEQ ID NOS: 12

<210> SEQ ID NO 1
<211> LENGTH: 19
<212> TYPE: DNA
<213> ORGANISM: Artificial Sequence
<220> FEATURE:
<223> OTHER INFORMATION: Target Sequence based on Arenavirus Sequence
<220> FEATURE:
<221> NAME/KEY: MOD_RES
<222> LOCATION: (6)..(6)
<223> OTHER INFORMATION: n = C or A
<220> FEATURE:
<221> NAME/KEY: MOD_RES
<222> LOCATION: (8)..(8)
<223> OTHER INFORMATION: n = A, G or T

<400> SEQUENCE: 1
cgcacngngg atcctaggc                                                 19

<210> SEQ ID NO 2
<211> LENGTH: 20
<212> TYPE: DNA
<213> ORGANISM: Artificial Sequence
<220> FEATURE:
<223> OTHER INFORMATION: Target Sequence based on Arenavirus Sequence

<400> SEQUENCE: 2
cgcctaggat ccccggtgcg                                                20

<210> SEQ ID NO 3
<211> LENGTH: 21
```

```
<210> SEQ ID NO 3
<211> LENGTH: 21
<212> TYPE: DNA
<213> ORGANISM: Artificial Sequence
<220> FEATURE:
<223> OTHER INFORMATION: Target Sequence based on Arenavirus Sequence

<400> SEQUENCE: 3
cgcctaggat ccccggtgcg c                                              21

<210> SEQ ID NO 4
<211> LENGTH: 20
<212> TYPE: DNA
<213> ORGANISM: Artificial Sequence
<220> FEATURE:
<223> OTHER INFORMATION: Target Sequence based on Arenavirus Sequence

<400> SEQUENCE: 4
gcctaggatc cactgtgcgc                                                20

<210> SEQ ID NO 5
<211> LENGTH: 19
<212> TYPE: DNA
<213> ORGANISM: Artificial Sequence
<220> FEATURE:
<223> OTHER INFORMATION: Target Sequence based on Arenavirus Sequence
<220> FEATURE:
<221> NAME/KEY: MOD_RES
<222> LOCATION: (12)..(14)
<223> OTHER INFORMATION: n = Inosine

<400> SEQUENCE: 5
gcctaggatc cncngtgcg                                                 19

<210> SEQ ID NO 6
<211> LENGTH: 20
<212> TYPE: DNA
<213> ORGANISM: Artificial Sequence
<220> FEATURE:
<223> OTHER INFORMATION: Target Sequence based on Arenavirus Sequence
<220> FEATURE:
<221> NAME/KEY: MOD_RES
<222> LOCATION: (13)..(15)
<223> OTHER INFORMATION: n = Inosine

<400> SEQUENCE: 6
cgcctaggat ccncngtgcg                                                20

<210> SEQ ID NO 7
<211> LENGTH: 13
<212> TYPE: PRT
<213> ORGANISM: Artificial Sequence
<220> FEATURE:
<223> OTHER INFORMATION: Synthetic arginine-rich peptide
<220> FEATURE:
<221> NAME/KEY: MOD_RES
<222> LOCATION: (12)..(12)
<223> OTHER INFORMATION: Xaa is 6-aminohexanoic acid
<220> FEATURE:
<221> NAME/KEY: MOD_RES
<222> LOCATION: (13)..(13)
<223> OTHER INFORMATION: Xaa is beta-alanine

<400> SEQUENCE: 7

Arg Arg Arg Arg Arg Arg Arg Arg Arg Phe Phe Xaa Xaa
1               5                   10

<210> SEQ ID NO 8
<211> LENGTH: 14
<212> TYPE: PRT
<213> ORGANISM: Artificial Sequence
```

```
<220> FEATURE:
<223> OTHER INFORMATION: Synthetic arginine-rich peptide
<220> FEATURE:
<221> NAME/KEY: MOD_RES
<222> LOCATION: (2)..(13)
<223> OTHER INFORMATION: Xaa is 6-aminohexanoic acid
<220> FEATURE:
<221> NAME/KEY: MOD_RES
<222> LOCATION: (14)..(14)
<223> OTHER INFORMATION: Xaa is beta-alanine

<400> SEQUENCE: 8

Arg Xaa Arg Arg Xaa Arg Arg Xaa Arg Arg Xaa Arg Xaa Xaa
1               5                   10

<210> SEQ ID NO 9
<211> LENGTH: 17
<212> TYPE: PRT
<213> ORGANISM: Artificial Sequence
<220> FEATURE:
<223> OTHER INFORMATION: Synthetic arginine-rich peptide
<220> FEATURE:
<221> NAME/KEY: MOD_RES
<222> LOCATION: (2)..(16)
<223> OTHER INFORMATION: Xaa is 6-aminohexanoic acid
<220> FEATURE:
<221> NAME/KEY: MOD_RES
<222> LOCATION: (17)..(17)
<223> OTHER INFORMATION: Xaa is beta-alanine

<400> SEQUENCE: 9

Arg Xaa Arg Xaa Arg Xaa Arg Xaa Arg Xaa Arg Xaa Arg Xaa Arg Xaa Xaa
1               5                   10                  15

<210> SEQ ID NO 10
<211> LENGTH: 9
<212> TYPE: PRT
<213> ORGANISM: Artificial Sequence
<220> FEATURE:
<223> OTHER INFORMATION: Synthetic arginine-rich peptide
<220> FEATURE:
<221> NAME/KEY: MOD_RES
<222> LOCATION: (2)..(8)
<223> OTHER INFORMATION: Xaa is 6-aminohexanoic acid
<220> FEATURE:
<221> NAME/KEY: MOD_RES
<222> LOCATION: (9)..(9)
<223> OTHER INFORMATION: Xaa is beta-alanine

<400> SEQUENCE: 10

Arg Xaa Arg Xaa Arg Xaa Arg Xaa Xaa
1               5

<210> SEQ ID NO 11
<211> LENGTH: 8
<212> TYPE: PRT
<213> ORGANISM: Artificial Sequence
<220> FEATURE:
<223> OTHER INFORMATION: Synthetic arginine-rich peptide
<220> FEATURE:
<221> NAME/KEY: MOD_RES
<222> LOCATION: (2)..(7)
<223> OTHER INFORMATION: Xaa is 6-aminohexanoic acid
<220> FEATURE:
<221> NAME/KEY: MOD_RES
<222> LOCATION: (8)..(8)
<223> OTHER INFORMATION: Xaa is beta-alanine

<400> SEQUENCE: 11

Arg Xaa Arg Arg Xaa Arg Xaa Xaa
1               5
```

```
<210> SEQ ID NO 12
<211> LENGTH: 11
<212> TYPE: PRT
<213> ORGANISM: Artificial Sequence
<220> FEATURE:
<223> OTHER INFORMATION: Synthetic arginine-rich peptide
<220> FEATURE:
<221> NAME/KEY: MOD_RES
<222> LOCATION: (2)..(10)
<223> OTHER INFORMATION: Xaa is 6-aminohexanoic acid
<220> FEATURE:
<221> NAME/KEY: MOD_RES
<222> LOCATION: (11)..(11)
<223> OTHER INFORMATION: Xaa is beta-alanine

<400> SEQUENCE: 12

Arg Xaa Arg Arg Xaa Arg Arg Xaa Arg Xaa Xaa
1               5                   10
```